US010368997B2

(12) United States Patent
Jones et al.

(10) Patent No.: US 10,368,997 B2
(45) Date of Patent: Aug. 6, 2019

(54) THREE-DIMENSIONAL LATTICE STRUCTURES FOR IMPLANTS

(71) Applicant: HD LifeSciences LLC, Woburn, MA (US)

(72) Inventors: Christopher L. Jones, Malden, MA (US); Ian Helmar, Beverly, MA (US); Lucas Diehl, Beverly, MA (US); Jason Tinley, Fort Worth, TX (US); Kevin D. Chappuis, Malden, MA (US); John F. Sullivan, Pelham, NH (US)

(73) Assignee: HD LifeSciences LLC, Woburn, MA (US)

( * ) Notice: Subject to any disclaimer, the term of this patent is extended or adjusted under 35 U.S.C. 154(b) by 0 days.

(21) Appl. No.: 15/876,695

(22) Filed: Jan. 22, 2018

(65) Prior Publication Data

US 2018/0280144 A1 Oct. 4, 2018

Related U.S. Application Data

(60) Provisional application No. 62/480,383, filed on Apr. 1, 2017, provisional application No. 62/480,393, filed on Apr. 1, 2017, provisional application No. 62/619,260, filed on Jan. 19, 2018.

(51) Int. Cl.

| A61F 2/00 | (2006.01) |
|---|---|
| A61F 2/30 | (2006.01) |
| A61C 13/00 | (2006.01) |
| A61F 2/44 | (2006.01) |
| A61F 2/28 | (2006.01) |
| A61L 27/50 | (2006.01) |
| A61L 27/56 | (2006.01) |
| A61C 8/00 | (2006.01) |
| B33Y 80/00 | (2015.01) |
| B29C 64/165 | (2017.01) |

(52) U.S. Cl.
CPC .......... *A61F 2/3094* (2013.01); *A61C 8/0013* (2013.01); *A61C 13/0019* (2013.01); *A61F 2/2846* (2013.01); *A61F 2/30771* (2013.01); *A61F 2/30907* (2013.01); *A61F 2/30942* (2013.01); *A61F 2/44* (2013.01); *A61L 27/505* (2013.01); *A61L 27/56* (2013.01); *B33Y 80/00* (2014.12); *A61F 2/30767* (2013.01); *A61F 2002/0081* (2013.01); *A61F 2002/30006* (2013.01); *A61F 2002/30014* (2013.01); *A61F 2002/30018* (2013.01); *A61F 2002/30069* (2013.01); *A61F 2002/3092* (2013.01); *A61F 2002/3093* (2013.01); *A61F 2002/30113* (2013.01); *A61F 2002/30141* (2013.01); *A61F 2002/30143* (2013.01); *A61F 2002/30148* (2013.01); *A61F 2002/30151* (2013.01); *A61F 2002/30156* (2013.01); *A61F 2002/30263* (2013.01); *A61F 2002/30273* (2013.01); *A61F 2002/30677* (2013.01); *A61F 2002/30766* (2013.01); *A61F 2002/30914* (2013.01); *A61F 2002/30919* (2013.01); *A61F 2002/30945* (2013.01); *A61F 2210/0057* (2013.01); *A61F 2240/001* (2013.01); *A61F 2310/00023* (2013.01); *A61L 2430/02* (2013.01); *B29C 64/165* (2017.08)

(58) Field of Classification Search
CPC ........................................................ A61F 2/00
See application file for complete search history.

(56) References Cited

U.S. PATENT DOCUMENTS

| 6,206,924 | B1 | 3/2001 | Timm |
|---|---|---|---|
| 8,697,231 | B2 | 4/2014 | Longepied et al. |
| 9,308,076 | B2 | 4/2016 | Ringeisen et al. |
| 9,456,901 | B2 | 10/2016 | Jones et al. |
| 2006/0147332 | A1 | 7/2006 | Jones et al. |
| 2007/0142914 | A1 | 6/2007 | Jones et al. |
| 2012/0177939 | A1 | 7/2012 | Longepied et al. |
| 2012/0215310 | A1 | 8/2012 | Sharp et al. |
| 2012/0321878 | A1 | 12/2012 | Landon et al. |
| 2014/0121776 | A1 | 5/2014 | Hunt |
| 2017/0014235 | A1 | 1/2017 | Jones et al. |

FOREIGN PATENT DOCUMENTS

| CN | 204971711 U | 1/2016 |
|---|---|---|
| WO | 9933641 | 7/1999 |
| WO | 2015164982 | 11/2015 |

OTHER PUBLICATIONS

International Search Report dated Jun. 1, 2018 from corresponding PCT/US2018/014720, pp. 3.
International Written Opinion dated Jun. 1, 2018 from corresponding PCT/US2018/014720, pp. 10.
Ahmadi, et al., Additively Manufactured Open-Cell Porous Biomaterials Made from Six Different Space-Filling Unit Cells: The Mechanical and Morphological Properties, Materials 2015, 8, 1871-1896.
Babaee, et al., Mechanical properties of open-cell rhombic dodecahedron cellular structures, Acta Materialia 60 (2012) 2873-2885.
Hoffmann, et al., Rapid prototyped porous nickel-titanium scaffolds as bone substitutes, Journal of Tissue Engineering vol. 5: 1-14, 2014, 1-14.
Nouri, Titanium foam scaffolds for dental applications, Chapter • Jan. 2017, DOI: 10.1016/8978-0-08-101289-5.00005-6, https://www.researchgate.net/publication/311398347, 131-160.

(Continued)

*Primary Examiner* — Christopher D. Prone
(74) *Attorney, Agent, or Firm* — Law Offices of Daniel A. Tesler, LLC; Reza M. Mollaaghababa; Ashley T. Brzezinski

(57) ABSTRACT

The three-dimensional lattice structures disclosed herein have applications including use in medical implants. Some examples of the lattice structure are structural in that they can be used to provide structural support or mechanical spacing. In some examples, the lattice can be configured as a scaffold to support bone or tissue growth. Some examples can use a repeating modified rhombic dodecahedron or radial dodeca-rhombus unit cell. The lattice structures are also capable of providing a lattice structure with anisotropic properties to better suit the lattice for its intended purpose.

22 Claims, 16 Drawing Sheets

(56) References Cited

OTHER PUBLICATIONS

Zhang, et al., Additively Manufactured Scaffolds for Bone Tissue Engineering and the Prediction of their Mechanical Behavior: A Review, Materials 2017, 10, 50, 1-28.

International Search Report and Written Opinion of the International Searching Authority, dated Jun. 1, 2008, in related case PCT/US2018/014720, 13 pages.

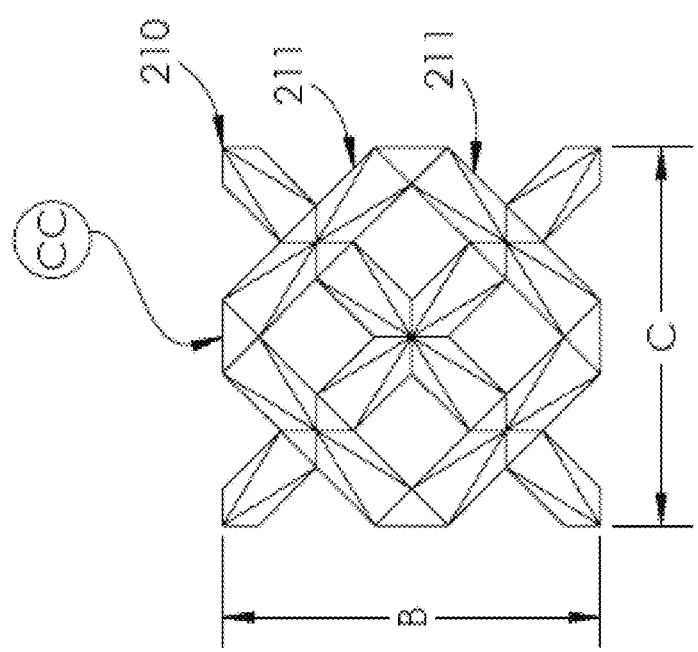

THREE-DIMENSIONAL LATTICE STRUCTURES FOR IMPLANTS

CROSS REFERENCE TO RELATED APPLICATIONS

This application claims the benefit of U.S. Provisional Patent Application No. 62/480,383 filed Apr. 1, 2017, U.S. Provisional Patent Application No. 62/480,393 filed Apr. 1, 2017, and U.S. Provisional Patent Application No. 62/619,260 filed Jan. 19, 2018, which are hereby incorporated by reference in its entirety.

FIELD OF THE INVENTION

The present invention relates to structures used in medical implants and, in particular, to structures characterized as a three-dimensional lattice or scaffold.

BACKGROUND OF THE INVENTION

Medical implants can be constructed using a wide range of materials, including metallic materials, Polyether ether ketone (hereinafter "PEEK"), ceramic materials and various other materials or composites thereof. There are competing priorities when selecting a material for an implant in order for the implant to pass regulatory testing. Some priorities when designing an implant could include strength, stiffness, fatigue resistance, radiolucency, and bioactivity. Therefore, when designing an implant to meet regulatory standards, oftentimes, some compromises have to be made to meet all testing requirements.

BRIEF SUMMARY OF THE INVENTION

In some embodiments, the present invention provides a lattice structure that can be useful in applications including medical implants. The present invention can also provide a lattice structure with anisotropic properties that can be used in medical implants and a method of use. In some embodiments, the lattice structures disclosed herein can be used to provide structural support or mechanical spacing. In other embodiments, the lattice structures disclosed herein can provide a scaffold for bone growth.

The structures described herein may be constructed from a range of materials with or without additional surface treatments or coatings. The lattice structures can use a repeating geometric pattern in some embodiments, where a unit cell can be repeated over a volume. Some unit cells that are disclosed include a modified rhombic dodecahedron unit cell and a radial dodeca-rhombus unit cell.

While the embodiments expressed herein are directed towards medical implants, the structures disclosed could also be beneficial when used in medical devices outside of the body that require a high strength compared to volumetric density. Other medical devices that could include one or more embodiments described herein include, but are not limited to, external casts or splints, prostheses, orthoses, ports, guides, markers, superstructures, or exoskeletons.

In particular, cancellous bone has anisotropic properties and possesses different mechanical properties in different directions. For instance, bone in the spine can be more stiff in the rostral-caudal direction so that a load that would fracture the bone in the anterior to posterior direction would only cause an elastic deformation in the rostral-caudal direction. Matching an implant's properties to the surrounding bone at an implant site is important because a mismatch in strength or stiffness can have an effect on the strength of new bone growth. According to Wolff's Law, bone will adapt to the physiological stresses put on it over time, becoming stronger in response when loaded and becoming weaker when not loaded. Therefore, reducing the load that a new bone formation experiences can reduce the mechanical strength of the new bone formation.

In some embodiments, the present invention provides biocompatible structures with anisotropic properties and a method of use. In particular, some embodiments of the present invention can be characterized as having an elastic modulus in one direction and at least a second elastic modulus in another direction. Directions, as used herein, are used in reference to the three-dimensional Cartesian coordinates where the x axis and y axis are horizontal and the z axis is vertical (also described herein as the x, y and z "direction"). The elastic modulus, when used to describe a lattice, implant or structure of any kind, refers to both or either of the design elastic modulus or the actual elastic modulus. The design elastic modulus of a lattice, implant or structure is the elastic modulus calculated based on its structural configuration and its material composition. The actual elastic modulus refers to the elastic modulus of a lattice, implant or structure after it has been manufactured. The actual elastic modulus can vary from the design elastic modulus due to changes or variations within manufacturing tolerances. For example, a lattice, implant or structure that is overbuilt within an acceptable tolerance during manufacturing could have a higher actual elastic modulus than the design elastic modulus. In many situations, the actual elastic modulus can be calculated using a correction factor, creating an approximate actual elastic modulus. An approximate actual elastic modulus generally quantifies the expected actual elastic modulus of a lattice, implant or structure when testing of a manufactured article has not been completed. Since a lattice, implant or structure of any kind can be easily designed using a design elastic modulus or to an approximate actual elastic modulus through the application of a correction factor, the use of the term "elastic modulus" herein can refer to both or either design parameter.

Some embodiments disclosed herein can be useful as a scaffold for bone growth. In some examples, the scaffolds can be structural, meaning that they provide structural support or mechanical spacing, and in other examples, the scaffolds can be nonstructural. In examples that use a structural scaffold, the material can provide support that more closely mimics the properties of naturally occurring bone. For instance, cancellous bone has anisotropic properties and it could be appropriate to use a lattice structure with anisotropic properties, as disclosed herein, as a bone growth scaffold in areas including the spine. The present invention can also be used in other applications where a scaffold for bone growth with different mechanical properties in at least two directions is desirable. In another example, it may be desirable for a scaffold to load bone in one or more directions of reduced stiffness and not in one or more directions of shielding or increased stiffness to promote preferential bone growth in the direction(s) of loading.

Many of the exemplary embodiments presented in this application are optimized for use as a scaffold for bone in spine, however, it is appreciated that the invention could be used with other types bone and other types of tissue within the inventive concept expressed herein.

In one exemplary embodiment of an anisotropic lattice structure is an elongated modified rhombic dodecahedron lattice that has been elongated in the x and y axes relative to the z axis. The elongated modified rhombic dodecahedron lattice is presented as a single cell defined by struts, with additional struts extending away from the cell to show portions of the repeating structure. The unit cell may be repeated in a lattice structure to achieve an open cell structure of the desired volume and mechanical properties.

In a second exemplary embodiment of an anisotropic lattice is a grouping of three elongated modified rhombic dodecahedron cells that have been elongated in the x and y axes relative to the z axis. The grouping is presented as three unit cells defined by struts, in a stacked arrangement, with additional struts extending away from the cell to show portions of the repeating structure.

The disclosed embodiments of the present invention can be used in a method of reducing stress shielding. It can be especially beneficial to reduce stress shielding in spinal fusion procedures. The anisotropic unit cells of the present invention can be repeated to form an anisotropic lattice or scaffold for use in spinal fusion procedures. The anisotropic lattice can provide mechanical spacing between the endplates of the adjacent vertebrae and provide a scaffold for bone growth. The anisotropic properties of the present invention can allow a reduced elastic modulus in the superior to inferior direction, allowing new bone growth to be subject to physiological forces of the load-bearing spine. The reduction in stress shielding can result in stronger new bone growth.

The anisotropic properties may allow reduced stiffness in one or more directions of bone growth while possessing the requisite stiffness in one or more directions of off-axis biomechanical loading and loading required for device testing. When elongating a unit cell in a direction, the elongation can change the strut angle and decrease the stiffness of the unit cell in a direction normal to the elongation.

BRIEF DESCRIPTION OF THE SEVERAL VIEWS OF THE DRAWINGS

FIG. 9 is a bottom view of a second exemplary embodiment of an anisotropic lattice structure, showing an alternate elongated modified rhombic dodecahedron lattice.

DETAILED DESCRIPTION OF THE INVENTION

Figure 1A:
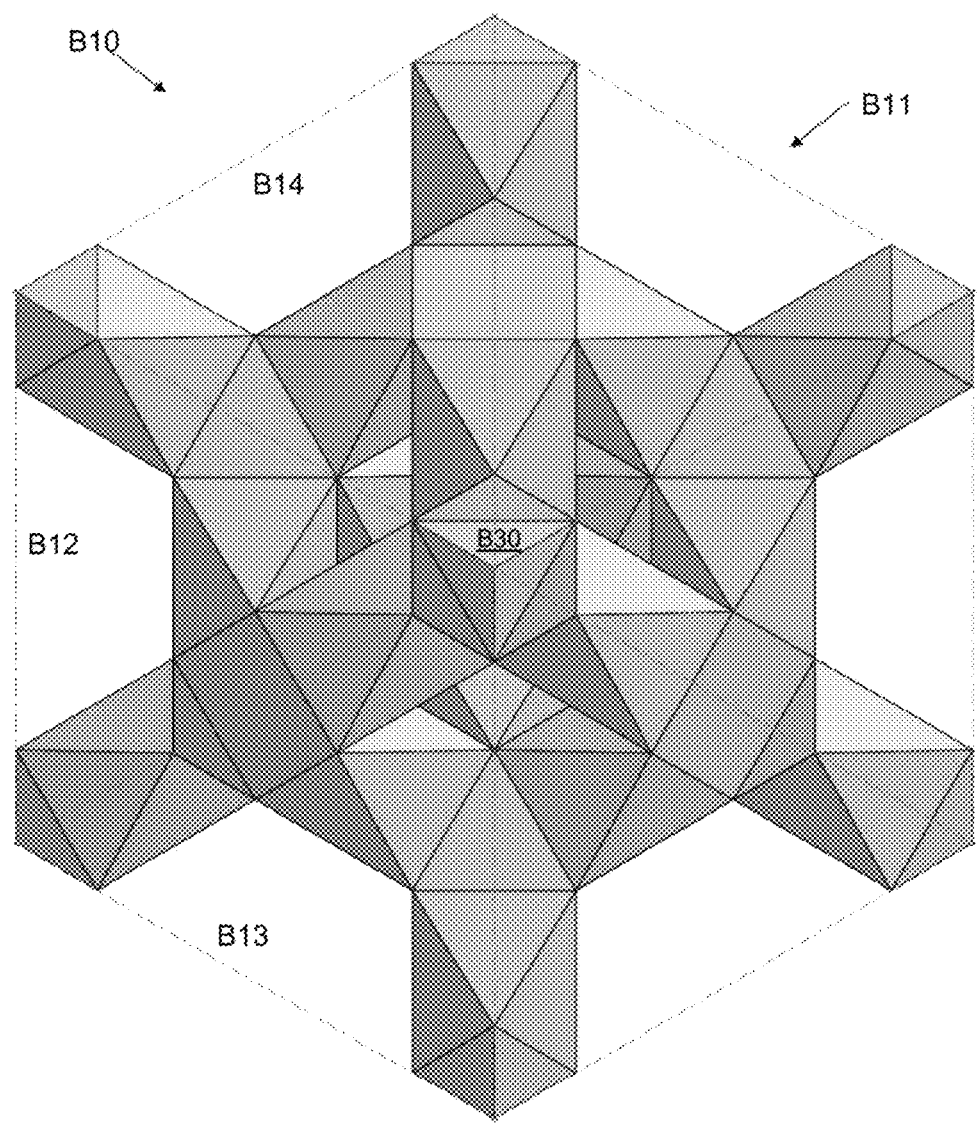
FIG. 1A is an isometric view of a single modified rhombic dodecahedron unit cell containing a full modified rhombic dodecahedron structure along with radial struts that comprise portions of adjacent unit cells.

In many situations, it is desirable to use an implant that is capable of bone attachment or osteointegration over time. It is also desirable in many situations to use an implant that is capable of attachment or integration with living tissue. Examples of implants where attachment to bone or osteointegration is beneficial include, but are not limited to, cervical, lumbar, and thoracic interbody fusion implants, vertebral body replacements, osteotomy wedges, dental implants, bone stems, acetabular cups, cranio-facial plating, bone replacement and fracture plating. In many applications, it is also desirable to stress new bone growth to increase its strength. According to Wolff's law, bone will adapt to stresses placed on it so that bone under stress will grow stronger and bone that isn't stressed will become weaker.

In some aspects, the systems and methods described herein can be directed toward implants that are configured for osteointegration and stimulating adequately stressed new bone growth. Many of the exemplary implants of the present invention are particularly useful for use in situations where it is desirable to have strong bone attachment and/or bone growth throughout the body of an implant. Whether bone growth is desired only for attachment or throughout an implant, the present invention incorporates a unique lattice structure that can provide mechanical spacing, a scaffold to support new bone growth and a modulus of elasticity that allows new bone growth to be loaded with physiological forces. As a result, the present invention provides implants that grow stronger and healthier bone for more secure attachment and/or for a stronger bone after the implant osteointegrates.

The exemplary embodiments of the invention presented can be comprised, in whole or in part, of a lattice. A lattice, as used herein, refers to a three-dimensional material with one or more interconnected openings that allow a fluid to communicate from one location to another location through an opening. A three-dimensional material refers to a material that fills a three-dimensional space (i.e. has height, width and length). Lattices can be constructed by many means, including repeating various geometric shapes or repeating random shapes to accomplish a material with interconnected openings. An opening in a lattice is any area within the bounds of the three-dimensional material that is devoid of that material. Therefore, within the three-dimensional boundaries of a lattice, there is a volume of material and a volume that is devoid of that material.

The material that provides the structure of the lattice is referred to as the primary material. The structure of a lattice does not need to provide structural support for any purpose, but rather refers to the configuration of the openings and interconnections that comprise the lattice. An opening in a lattice may be empty, filled with a gaseous fluid, filled with a liquid fluid, filled with a solid or partially filled with a fluid and/or solid. Interconnections, with respect to openings, refer to areas devoid of the primary material and that link at least two locations together. Interconnections may be configured to allow a fluid to pass from one location to another location.

A lattice can be defined by its volumetric density, meaning the ratio between the volume of the primary material and the volume of voids presented as a percentage for a given three-dimensional material. The volume of voids is the difference between the volume of the bounds of the three-dimensional material and the volume of the primary material. The volume of voids can comprise of the volume of the openings, the volume of the interconnections and/or the volume of another material present. For example, a lattice with a 30% volumetric density would be comprised of 30% primary material by volume and 70% voids by volume over a certain volume. A lattice with a 90% volumetric density would be comprised of 90% primary material by volume and 10% voids by volume over a certain volume. In three-dimensional materials with a volumetric density of less than 50%, the volume of the primary material is less than the volume of voids. While the volumetric density refers to the volume of voids, the voids do not need to remain void and can be filled, in whole or in part, with a fluid or solid prior to, during or after implantation.

Lattices comprised of repeating geometric patterns can be described using the characteristics of a repeating unit cell. A unit cell in a repeating geometric lattice is a three-dimensional shape capable of being repeated to form a lattice. A repeating unit cell can refer to multiple identical unit cells that are repeated over a lattice structure or a pattern through all or a portion of a lattice structure. Each unit cell is comprised of a certain volume of primary material and a certain void volume, or in other words, a spot volumetric density. The spot volumetric density may cover as few as a partial unit cell or a plurality of unit cells. In many situations, the spot volumetric density will be consistent with the material's volumetric density, but there are situations where it could be desirable to locally increase or decrease the spot volumetric density.

Unit cells can be constructed in numerous volumetric shapes containing various types of structures. Unit cells can be bound by a defined volume of space to constrict the size of the lattice structure or other type of structure within the unit cell. In some embodiments, unit cells can be bound by volumetric shapes, including but not limited to, a cubic volume, a cuboid volume, a hexahedron volume or an amorphous volume. The unit cell volume of space can be defined based on a number of faces that meet at corners. In examples where the unit cell volume is a cubic, cuboid or hexahedron volume, the unit cell volume can have six faces and eight corners, where the corners are defined by the location where three faces meet. Unit cells may be interconnected in some or all areas, not interconnected in some or all areas, of a uniform size in some or all areas or of a nonuniform size in some or all areas. In some embodiments disclosed herein that use a repeating geometric pattern, the unit cells can be defined by a number of struts defining the edges of the unit cell and joined at nodes about the unit cell. Unit cells so defined can share certain struts among more than one unit cell, so that two adjacent unit cells may share a common planar wall defined by struts common to both cells. In some embodiments disclosed herein that use a repeating geometric pattern, the unit cells can be defined by a node and a number of struts extending radially from that node.

While the present application uses volumetric density to describe exemplary embodiments, it is also possible to describe them using other metrics, including but not limited to cell size, strut size or stiffness. Cell size may be defined using multiple methods, including but not limited to cell diameter, cell width, cell height and cell volume. Strut size may be defined using multiple methods, including but not limited to strut length and strut diameter.

Repeating geometric patterns are beneficial for use in lattice structures contained in implants because they can provide predictable characteristics. Many repeating geometric shapes may be used as the unit cell of a lattice, including but are not limited to, rhombic dodecahedron, diamond, dodecahedron, square, pentagonal, hexagonal, octagonal, sctet struts, trunic octa, diagonal struts, other known geometric structures, and rounded, reinforced, weakened, or simplified versions of each geometry.

Lattices may also be included in implants as a structural component or a nonstructural component. Lattices used in structural applications may be referred to herein as structural lattices, load-bearing lattices or stressed lattices. In some instances, structural lattices, load-bearing lattices or stressed lattices may be simply referred to as a lattice. Repeating geometric shaped unit cells, particularly the rhombic dodecahedron, are well suited, in theory, for use in structural lattices because of their strength to weight ratio. To increase the actual strength and fatigue resistance of a rhombic dodecahedron lattice, the present invention, in some embodiments, includes a modified strut comprised of triangular segments, rather than using a strut with a rectangular or circular cross section. Some embodiments herein also modify the angles defining the rhombic faces of a rhombic dodecahedron to change the lattice's elastic modulus and fatigue resistance. The use of triangular segments provides a lattice with highly predictable printed properties that approach the theoretical strength values for a rhombic dodecahedron lattice.

In structural lattice applications, the strength and elastic modulus of the lattice can be approximated by the volumetric density. When the volumetric density increases, the strength and the elastic modulus increases. Compared to other porous structures, the lattice of the present invention has a higher strength and elastic modulus for a given volumetric density because of its ability to use the high strength to weight benefits of a rhombic dodecahedron, modified rhombic dodecahedron or radial dodeca-rhombus unit cell.

When configured to provide support for bone or tissue growth, a lattice may be referred to as a scaffold. Lattices can be configured to support bone or tissue growth by controlling the size of the openings and interconnections disposed within the three-dimensional material. A scaffold, if used on the surface of an implant, may provide an osteointegration surface that allows adjacent bone to attach to the implant. A scaffold may also be configured to provide a path that allows bone to grow further than a mere surface attachment. Scaffolds intended for surface attachment are referred to herein as surface scaffolds. A surface scaffold may be one or more unit cells deep, but does not extend throughout the volume of an implant. Scaffolds intended to support in-growth beyond mere surface attachment are referred to herein as bulk scaffolds. Scaffolds may also be included in implants as a structural component or a non-structural component. Scaffolds used in structural applications may be referred to herein as structural scaffolds, load-bearing scaffolds or stressed scaffolds. In some instances, structural scaffolds, load-bearing scaffolds or stressed scaffolds may be simply referred to as a scaffold. In some instances, the use of the term scaffold may refer to a material configured to provide support for bone or tissue growth, where the material is not a lattice.

The scaffolds described herein can be used to promote the attachment or in-growth of various types of tissue found in living beings. As noted earlier, some embodiments of the scaffold are configured to promote bone attachment and in-growth. The scaffolds can also be configured to promote attachment of in-growth of other areas of tissue, such as fibrous tissue. In some embodiments, the scaffold can be configured to promote the attachment or in-growth of multiple types of tissue. Some embodiments of the scaffolds are configured to be implanted near or abutting living tissue. Near living tissue includes situations where other layers, materials or coatings are located between a scaffold and any living tissue.

In some embodiments, the present invention uses bulk scaffolds with openings and interconnections that are larger than those known in the art. Osteons can range in diameter from about 100 μm and it is theorized that a bundle of osteons would provide the strongest form of new bone growth. Bone is considered fully solid when it has a diameter of greater than 3 mm so it is theorized that a bundle of osteons with a diameter equaling approximately half of that value would provide significant strength when grown within a scaffold. It is also theorized that osteons may grow in irregular shapes so that the cross-sectional area of an osteon could predict its strength. A cylindrical osteon growth with a 3 mm diameter has a cross-sectional area of approximately 7 square mm and a cylindrical osteon with a 1.5 mm diameter has a cross-sectional area of 1.8 square mm. It is theorized that an osteon of an irregular shape with a cross-sectional area of at least 1.8 square millimeters could provide a significant strength advantage when grown in a scaffold.

Most skilled in the art would indicate that pores or openings with a diameter or width between 300 μm to 900 μm, with a pore side of 600 μm being ideal, provide the best scaffold for bone growth. Instead, some embodiments of the present invention include openings and interconnections with a diameter or width on the order of 1.0 to 15.0 times the known range, with the known range being 300 μm to 900 μm, resulting in openings from 0.07 mm$^2$ up to 145 mm$^2$ cross sectional area for bone growth. In some examples, pores or openings with a diameter or width between and including 100 μm to 300 μm could be beneficial. Some examples include openings and interconnections with a diameter on the order of 1.0 to 5.0 times the known range. It has been at least theorized that the use of much larger openings and interconnections than those known in the art will allow full osteons and solid bone tissue to form throughout the bulk scaffold, allowing the vascularization of new, loadable bone growth. In some examples, these pores may be 3 mm in diameter or approximately 7 mm$^2$ in cross sectional area. In other examples, the pores are approximately 1.5 mm in diameter or approximately 1.75 mm$^2$ in cross sectional area. The use of only the smaller diameter openings and interconnections known in the art are theorized to limit the penetration of new bone growth into a bulk scaffold because the smaller diameter openings restrict the ability of vascularization throughout the bulk scaffold.

A related structure to a lattice is a closed cell material. A closed cell material is similar to a lattice, in that it has openings contained within the bounds of a three-dimensional material, however, closed cell materials generally lack interconnections between locations through openings or other pores. A closed cell structure may be accomplished using multiple methods, including the filling of certain cells or through the use of solid walls between the struts of unit cells. A closed cell structure can also be referred to as a cellular structure. It is possible to have a material that is a lattice in one portion and a closed cell material in another. It is also possible to have a closed cell material that is a lattice with respect to only certain interconnections between openings or vice versa. While the focus of the present disclosure is on lattices, the structures and methods disclosed herein can be easily adapted for use on closed cell structures within the inventive concept.

The lattice used in the present invention can be produced from a range of materials and processes. When used as a scaffold for bone growth, it is desirable for the lattice to be made of a biocompatible material that allows for bone attachment, either to the material directly or through the application of a bioactive surface treatment. In one example, the scaffold is comprised of an implantable metal. Implantable metals include, but are not limited to, zirconium, stainless steel (316 & 316L), tantalum, nitinol, cobalt chromium alloys, titanium and tungsten, and alloys thereof. Scaffolds comprised of an implantable metal may be produced using an additive metal fabrication or 3D printing process. Appropriate production processes include, but are not limited to, direct metal laser sintering, selective laser sintering, selective laser melting, electron beam melting, laminated object manufacturing and directed energy deposition.

In another example, the lattice of the present invention is comprised of an implantable metal with a bioactive coating. Bioactive coatings include, but are not limited to, coatings to accelerate bone growth, anti-thrombogenic coatings, anti-microbial coatings, hydrophobic or hydrophilic coatings, and hemophobic, superhemophobic, or hemophilic coatings. Coatings that accelerate bone growth include, but are not limited to, calcium phosphate, hydroxyapatite ("HA"), silicate glass, stem cell derivatives, bone morphogenic proteins, titanium plasma spray, titanium beads and titanium mesh. Anti-thrombogenic coatings include, but are not limited to, low molecular weight fluoro-oligomers. Anti-microbial coatings include, but are not limited to, silver, organosilane compounds, iodine and silicon-nitride. Superhemophobic coatings include fluorinated nanotubes.

In another example, the lattice is made from a titanium alloy with an optional bioactive coating. In particular, Ti6Al4V ELI wrought (American Society for Testing and Materials ("ASTM") F136) is a particularly well-suited titanium alloy for scaffolds. While Ti6Al4V ELI wrought is the industry standard titanium alloy used for medical purposes, other titanium alloys, including but not limited to, unalloyed titanium (ASTM F67), Ti6Al4V standard grade (ASTM F1472), Ti6Al7Nb wrought (ASTM 1295), Ti5Al2.5Fe wrought (British Standards Association/International Standard Organization Part 10), CP and Ti6Al4V standard grade powders (ASTM F1580), Ti13Nb13Zr wrought (ASTM F1713), the lower modulus Ti-24Nb-4Zr-8Sn and Ti12Mo6Zr2Fe wrought (ASTM F1813) can be appropriate for various embodiments of the present invention.

Titanium alloys are an appropriate material for scaffolds because they are biocompatible and allow for bone attachment. Various surface treatments can be done to titanium alloys to increase or decrease the level of bone attachment. Bone will attach to even polished titanium, but titanium with a surface texture allows for greater bone attachment. Methods of increasing bone attachment to titanium may be produced through a forging or milling process, sandblasting, acid etching, and the use of a bioactive coating. Titanium parts produced with an additive metal fabrication or 3D printing process, such as direct metal laser sintering, can be treated with an acid bath to reduce surface stress risers, normalize surface topography, and improve surface oxide layer, while maintaining surface roughness and porosity to promote bone attachment.

Additionally, Titanium or other alloys may be treated with heparin, heparin sulfate (HS), glycosaminoglycans (GAG), chondroitin-4-sulphate (C4S), chondroitin-6-sulphate (C6S), hyaluronan (HY), and other proteoglycans with or without an aqueous calcium solution. Such treatment may occur while the material is in its pre-manufacturing form (often powder) or subsequent to manufacture of the structure.

While a range of structures, materials, surface treatments and coatings have been described, it is believed that a lattice using a repeating modified rhombic dodecahedron (hereinafter "MRDD") unit cell can present a preferable combination of stiffness, strength, fatigue resistance, and conditions for bone ingrowth. In some embodiments, the repeating MRDD lattice is comprised of titanium or a titanium alloy. A generic rhombic dodecahedron (hereinafter "RDD"), by definition, has twelve sides in the shape of rhombuses. When repeated in a lattice, an RDD unit cell is comprised of 24 struts that meet at 14 vertices. The 24 struts define the 12 planar faces of the structure and disposed at the center of each planar face is an opening, or interconnection, allowing communication from inside the unit cell to outside the unit cell.

Figure 1B:
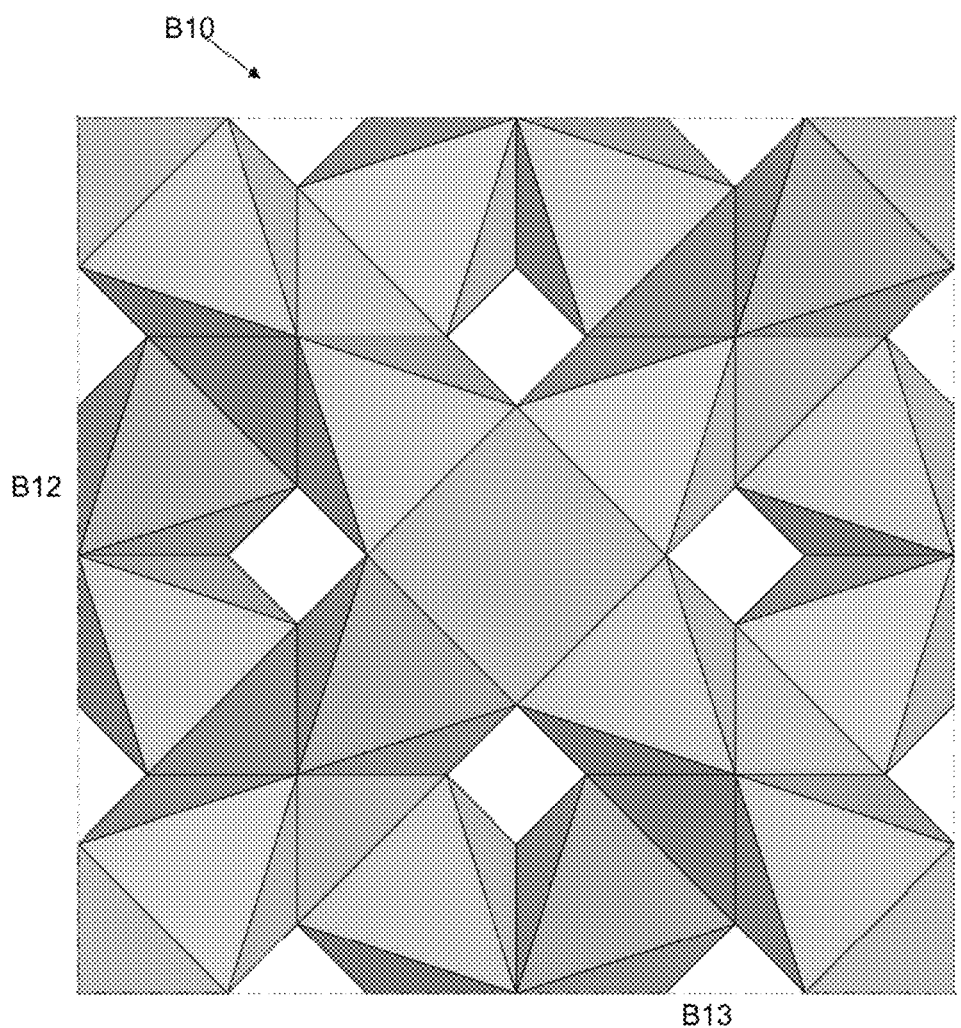
FIG. 1B is a side view of a single modified rhombic dodecahedron unit cell showing the configuration of interconnections when viewed from a lateral direction.

An example of the MRDD unit cell B10 used in the present invention is shown in FIGS. 1A-1E. In FIG. 1A is an isometric view of a single MRDD unit cell B10 containing a full MRDD structure along with radial struts that comprise portions of adjacent unit cells. In FIG. 1B is a side view of a single MRDD unit cell B10 showing the configuration of interconnections when viewed from a lateral direction. A top or bottom view of the MRDD unit cell B10 would be substantially the same as the side view depicted in FIG. 1B. The MRDD unit cell B10 differs in both structural characteristics and method of design from generic RDD shapes. A generic RDD is comprised of 12 faces where each face is an identical rhombus with an acute angle of 70.5 degrees and an obtuse angle of 109.5 degrees. The shape of the rhombus faces in a generic RDD do not change if the size of the unit cell or the diameter of the struts are changed because the struts are indexed based on their axis and each pass through the center of the 14 nodes or vertices.

In some embodiments of the MRDD, each node is contained within a fixed volume that defines its bounds and provides a fixed point in space for the distal ends of the struts. The fixed volume containing the MRDD or a sub-unit cell of the MRDD can be various shapes, including but not limited to, a cubic, cuboid, hexahedron or amorphous volume. Some examples use a fixed volume with six faces and eight corners defined by locations where three faces meet. The orientation of the struts can be based on the center of a node face at its proximate end and the nearest corner of the volume to that node face on its distal end. Each node is preferably an octahedron, more specifically a square bipyramid (i.e. a pyramid and inverted pyramid joined on a horizontal plane). Each node, when centrally located in a cuboid volume, more preferably comprises a square plane parallel to a face of the cuboid volume, six vertices and is oriented so that each of the six vertices are positioned at their closest possible location to each of the six faces of the cuboid volume. Centrally located, with regards to the node's location within a volume refers to positioning the node at a location substantially equidistant from opposing walls of the volume. In some embodiments, the node can have a volumetric density of 100 percent and in other embodiments, the node can have a volumetric density of less than 100 percent. Each face of the square bipyramid node can be triangular and each face can provide a connection point for a strut.

The struts can also be octahedrons, comprising an elongate portion of six substantially similar elongate faces and two end faces. The elongate faces can be isosceles triangles with a first internal angle, angle A, and a second internal angle, angle B, where angle B is greater than angle A. The end faces can be substantially similar isosceles triangles to one another with a first internal angle, angle C, and a second internal angle, angle D, where angle D is greater than angle C. Preferably, angle C is greater than angle A.

The strut direction of each strut is a line or vector defining the orientation of a strut and it can be orthogonal or non-orthogonal relative to the planar surface of each node face. In the MRDD and radial dodeca-rhombus structures disclosed herein, the strut direction can be determined using a line extending between the center of the strut end faces, the center of mass along the strut or an external edge or face of the elongate portion of the strut. When defining a strut direction using a line extending between the center of the strut end faces, the line is generally parallel to the bottom face or edge of the strut. When defining a strut direction using a line extending along the center of mass of the strut, the line can be nonparallel to the bottom face or edge of the strut. The octahedron nodes of the MRDD can be scaled to increase or decrease volumetric density by changing the origin point and size of the struts. The distal ends of the struts, however, are locked at the fixed volume corners formed about each node so that their angle relative to each node face changes as the volumetric density changes. Even as the volumetric density of an MRDD unit cell changes, the dimensions of the fixed volume formed about each node does not change. In FIG. 1A, dashed lines are drawn between the corners of the MRDD unit cell B10 to show the cube B11 that defines its bounds. In the MRDD unit cell in FIG. 1A, the height B12, width B13 and depth B14 of the unit cell are substantially the same, making the area defined by B11 a cube.

In some embodiments, the strut direction of a strut can intersect the center of the node and the corner of the cuboid volume nearest to the node face where the strut is fixed. In some embodiments, the strut direction of a strut can intersect just the corner of the cuboid volume nearest to the node face where the strut is fixed. In some embodiments, a reference plane defined by a cuboid or hexahedron face is used to describe the strut direction of a strut. When the strut direction of a strut is defined based on a reference plane, it can be between 0 degrees and 90 degrees from the reference plane. When the strut direction of a strut is defined based on a reference plane, it is preferably eight degrees to 30 degrees from the reference plane.

By indexing the strut orientation to a variable node face on one end and a fixed point on its distal end, the resulting MRDD unit cell can allow rhombus shaped faces with a smaller acute angle and larger obtuse angle than a generic RDD. The rhombus shaped faces of the MRDD can have two substantially similar opposing acute angles and two substantially similar opposing obtuse angles. In some embodiments, the acute angles are less than 70.5 degrees and the obtuse angles are greater than 109.5 degrees. In some embodiments, the acute angles are between 0 degrees and 55 degrees and the obtuse angles are between 125 degrees and 180 degrees. In some embodiments, the acute angles are between 8 degrees and 60 degrees and the obtuse angles are between 120 degrees and 172 degrees. The reduction in the acute angles increases fatigue resistance for loads oriented across the obtuse angle corner to far obtuse angle corner. The reduction in the acute angles and increase in obtuse angles also orients the struts to increase the MRDD's strength in shear and increases the fatigue resistance. By changing the rhombus corner angles from a generic RDD, shear loads pass substantially in the axial direction of some struts, increasing the shear strength. Changing the rhombus corner angles from a generic RDD also reduces overall deflection caused by compressive loads, increasing the fatigue strength by resisting deflection under load.

Figure 1C:
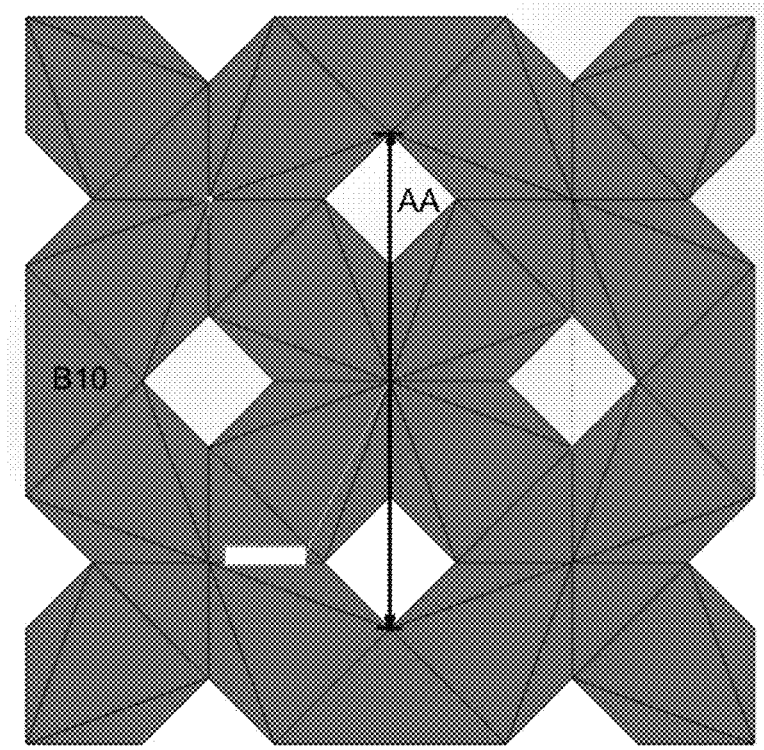
FIG. 1C is a side view of a single modified rhombic dodecahedron unit cell where the central void is being measured using the longest dimension method.
Figure 1D:
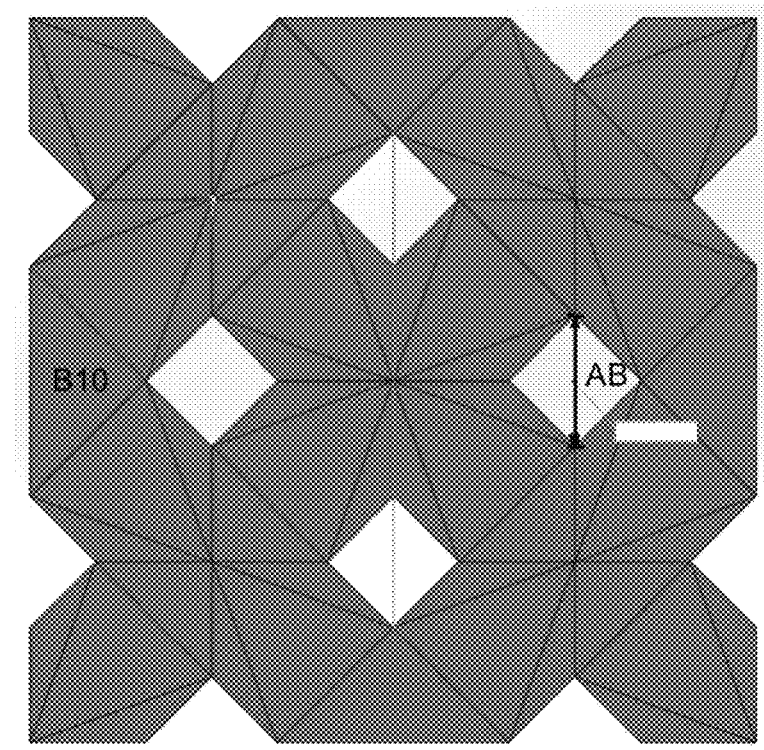
FIG. 1D is a side view of a single modified rhombic dodecahedron unit cell where an interconnection is being measured using the longest dimension method.

When placed towards the center of a lattice structure, the 12 interconnections of a unit cell connect to 12 different adjacent unit cells, providing continuous paths through the lattice. The size of the central void and interconnections in the MRDD may be defined using the longest dimension method as described herein. Using the longest dimension method, the central void can be defined by taking a measurement of the longest dimension as demonstrated in FIG. 1C. In FIG. 1C, the longest dimension is labeled as distance AA. The distance AA can be taken in the vertical or horizontal directions (where the directions reference the directions on the page) and would be substantially the same in this example. The interconnections may be defined by their longest measurement when viewed from a side, top or bottom of a unit cell. In FIG. 1D, the longest dimension is labeled as distance AB. The distance AB can be taken in the vertical or horizontal directions (where the directions reference the directions on the page). The view in FIG. 1D is a lateral view, however, in this example the unit cell will appear substantially the same when viewed from the top or bottom.

Figure 1E:
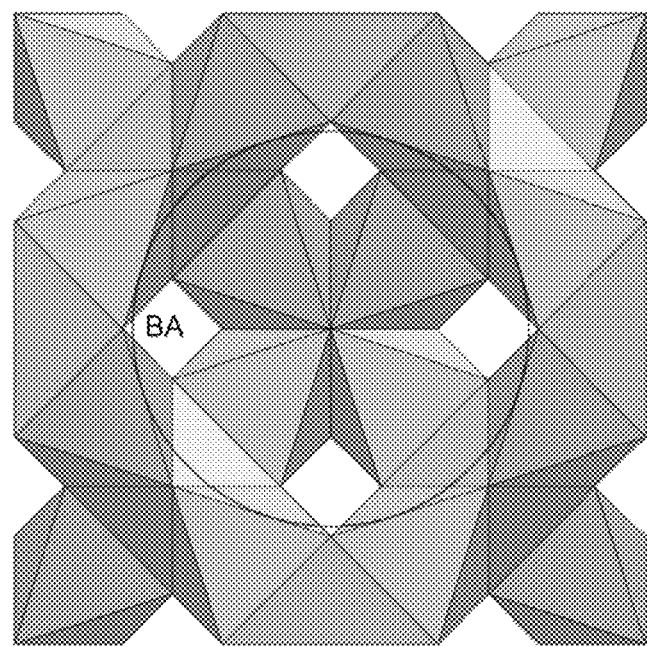
FIG. 1E is a side view of the central void of a modified rhombic dodecahedron unit cell being measured with the largest sphere method.
Figure 1F:
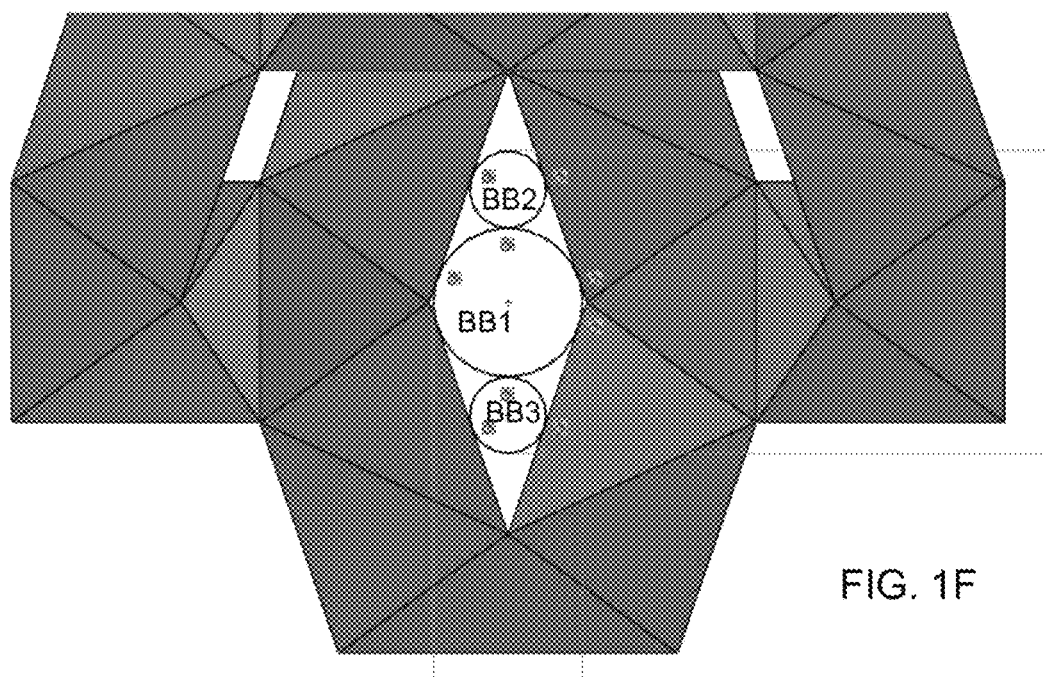
FIG. 1F is a view from a direction normal to the planar direction of an interconnection being measured with the largest sphere method.

The size of the central void and interconnections can alternatively be defined by the largest sphere method as described herein. Using the largest sphere method, the central void can be defined by the diameter of the largest sphere that can fit within the central void without intersecting the struts. In FIG. 1E is an example of the largest sphere method being used to define the size of a central void with a sphere with a diameter of BA. The interconnections are generally rhombus shaped and their size can alternatively be defined by the size of the length and width of three circles drawn within the opening. Drawn within the plane defining a side, a first circle BB1 is drawn at the center of the opening so that it is the largest diameter circle that can fit without intersecting the struts. A second circle BB2 and third circle BB3 is them drawn so that they are tangential to the first circle BB1 and the largest diameter circles that can fit without intersecting the struts. The diameter of the first circle BB1 is the width of the interconnection and the sum of the diameters of all three circles BB1, BB2 & BB3 represents the length of the interconnection. Using this method of measurement removes the acute corners of the rhombus shaped opening from the size determination. In some instances, it is beneficial to remove the acute corners of the rhombus shaped opening from the calculated size of the interconnections because of the limitations of additive manufacturing processes. For example, if an SLS machine has a resolution of 12 μm where the accuracy is within 5 μm, it is possible that the acute corner could be rounded by the SLS machine, making it unavailable for bone ingrowth. When designing lattices for manufacture on less precise additive process equipment, it can be helpful to use this measuring system to better approximate the size of the interconnections.

Using the alternative measuring method, in some examples, the width of the interconnections is approximately 600 μm and the length of the interconnections is approximately 300 μm. The use of a 600 μm length and 300 μm width provides an opening within the known pore sizes for bone growth and provides a surface area of roughly 1.8 square millimeters, allowing high strength bone growth to form. Alternative embodiments may contain interconnections with a cross sectional area of 1.0 to 15.0 times the cross-sectional area of a pore with a diameter of 300 μm. Other embodiments may contain interconnections with a cross sectional area of 1.0 to 15.0 times the cross-sectional area of a pore with a diameter of 900 μm.

The MRDD unit cell also has the advantage of providing at least two sets of substantially homogenous pore or opening sizes in a lattice structure. In some embodiments, a first set of pores have a width of about 200 μm to 900 μm and a second set of pores have a width of about 1 to 15 times the width of the first set of pores. In some embodiments, a first set of pores can be configured to promote the growth of osteoblasts and a second set of pores can be configured to promote the growth of osteons.

Pores sized to promote osteoblast growth can have a width of between and including about 100 μm to 900 μm. In some embodiments, pores sized to promote osteoblast growth can have a width that exceeds 900 μm. Pores sized to promote the growth of osteons can have a width of between and including about 100 μm to 13.5 mm. In some embodiments, pores sized to promote osteon growth can have a width that exceeds 13.5 mm.

In some embodiments, it is beneficial to include a number of substantially homogenous larger pores and a number of substantially homogenous smaller pores, where the number of larger pores is selected based on a ratio relative to the number of smaller pores. For example, some embodiments have one large pore for every one to 25 small pores in the lattice structure. Some embodiments preferably have one large pore for every eight to 12 smaller pores. In some embodiments, the number of larger and smaller pores can be selected based on a percentage of the total number of pores in a lattice structure. For example, some embodiments can include larger pores for four percent to 50 percent of the total number of pores and smaller pores for 50 percent to 96 percent of the total number of pores. More preferably, some embodiments can include larger pores for about eight percent to 13 percent of the total number of pores and smaller pores for about 87 percent to 92 percent of the total number of pores. It is believed that a lattice constructed with sets of substantially homogenous pores of the disclosed two sizes provides a lattice structure that simultaneously promotes osteoblast and osteon growth.

The MRDD unit cell may also be defined by the size of the interconnections when viewed from a side, top or bottom of a unit cell. The MRDD unit cell has the same appearance when viewed from a side, top or bottom, making the measurement in a side view representative of the others. When viewed from the side, as in FIG. 1D, an MRDD unit cell displays four distinct diamond shaped interconnections with substantially right angles. The area of each interconnection is smaller when viewed in the lateral direction than from a direction normal to the planar direction of each interconnection, but the area when viewed in the lateral direction can represent the area available for bone to grow in that direction. In some embodiments, it may be desirable to index the properties of the unit cell and lattice based on the area of the interconnections when viewed from the top, bottom or lateral directions.

In some embodiments of the lattice structures disclosed herein, the central void is larger than the length or width of the interconnections. Because the size of each interconnection can be substantially the same in a repeating MRDD structure, the resulting lattice can be comprised of openings of at least two discrete sizes. In some embodiments, it is preferable for the diameter of the central void to be approximately two times the length of the interconnections. In some embodiments, it is preferable for the diameter of the central void to be approximately four times the width of the interconnections.

In some embodiments, the ratio between the diameter of the central void and the length or width of the interconnections can be changed to create a structural lattice of a particular strength. In these embodiments, there is a correlation where the ratio between the central void diameter and the length or width of the interconnections increases as the strength of the structural lattice increases.

Figure 1G:
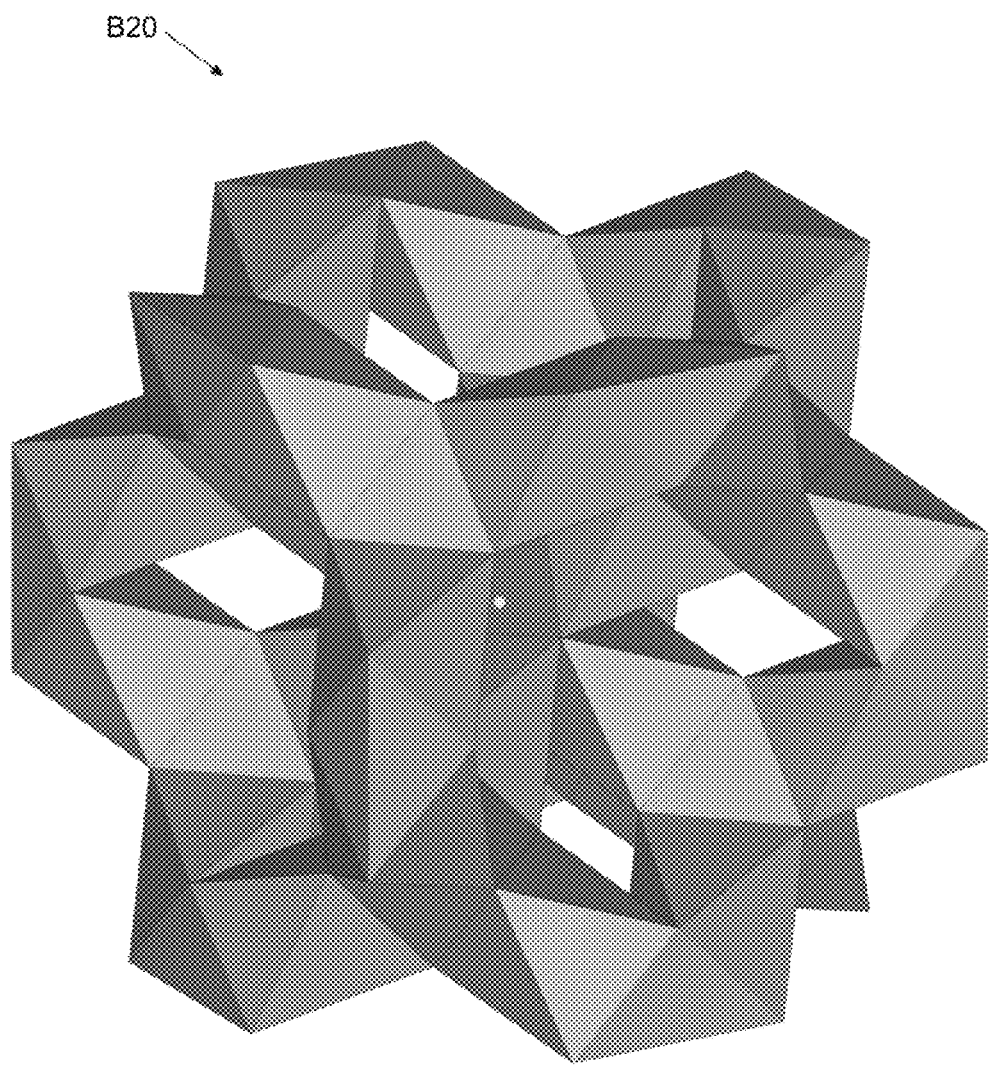
FIG. 1G is an isometric view of a single radial dodeca-rhombus unit cell.
Figure 1H:
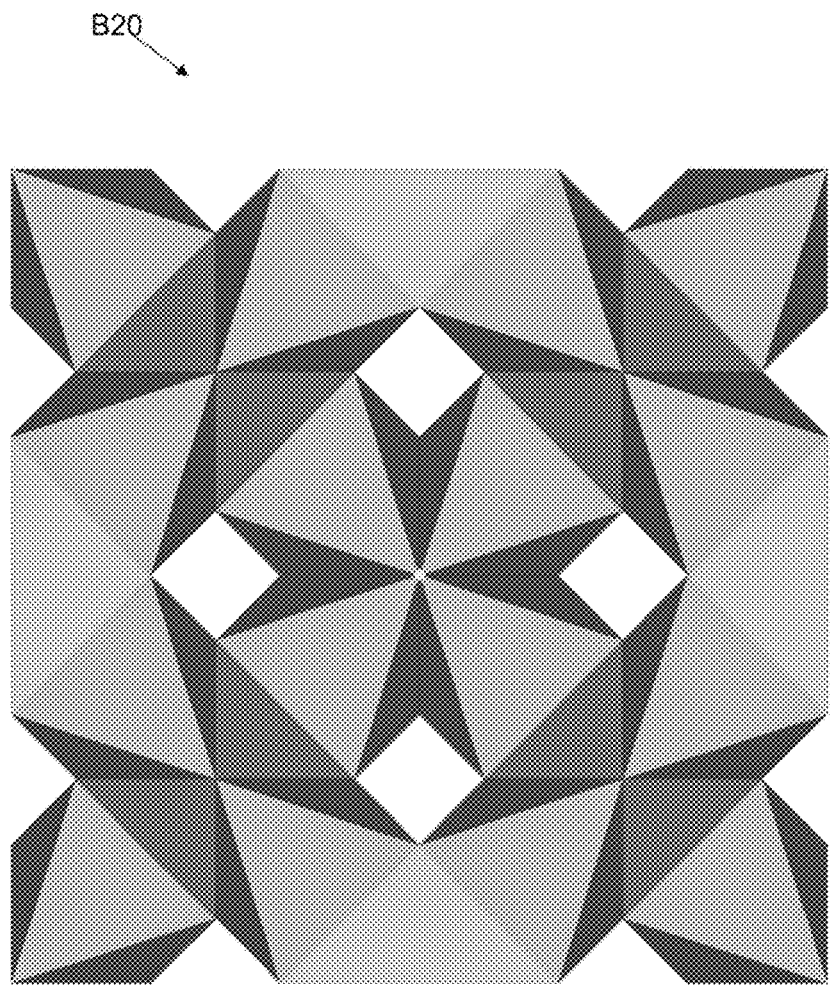
FIG. 1H is a side view of a single radial dodeca-rhombus unit cell.

It is also believed that a lattice using a repeating radial dodeca-rhombus (hereinafter "RDDR") unit cell can present a preferable combination of stiffness, strength, fatigue resistance, and conditions for bone ingrowth. In some embodiments, the repeating RDDR lattice is comprised of titanium or a titanium alloy. In FIG. 1G is an isometric view of a single RDDR unit cell B20 containing a full RDDR structure. In FIG. A8 is a side view of a single RDDR unit cell B20 showing the configuration of interconnections when viewed from a lateral direction. A top or bottom view of the RDDR unit cell B20 would be substantially the same as the side view depicted in FIG. A8.

As used herein, an RDDR unit cell B20 is a three-dimensional shape comprised of a central node with radial struts and mirrored struts thereof forming twelve rhombus shaped structures. The node is preferably an octahedron, more specifically a square bipyramid (i.e. a pyramid and inverted pyramid joined on a horizontal plane). Each face of the node is preferably triangular and fixed to each face is a strut comprised of six triangular facets and two end faces. The central axis of each strut can be orthogonal or non-orthogonal relative to the planar surface of each node face. The central axis may follow the centroid of the strut. The RDDR is also characterized by a central node with one strut attached to each face, resulting in a square bipyramid node with eight struts attached.

Figure 1I:
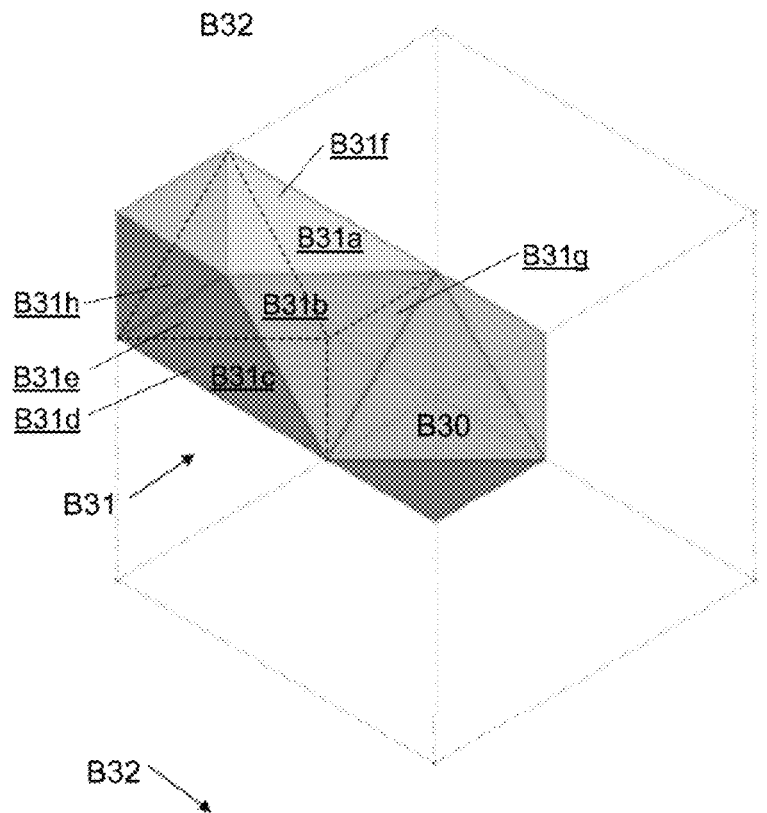
FIG. 1I is an isometric view of an example of a single node and single strut combination that could be used in a radial dodeca-rhombus unit cell.

Examples of node and strut combinations are shown in FIGS. 1I-1M. In FIG. 1I is an isometric view of a single node B30 with a single strut B31 attached. The node B30 is a square bipyramid oriented so that two peaks face the top and bottom of a volume B32 defining the bounds of the node B30 and any attached strut(s) B31. The node B30 is oriented so that the horizontal corners are positioned at their closest point to the lateral sides of the volume B32. The strut B31 extends from a node B30 face to the corner of the volume B32 defining the bounds of the node and attached struts. In FIG. 1I, the central axis of the strut is 45 degrees above the horizontal plane where the node's planar face is 45 degrees above a horizontal plane.

FIG. 1I also details an octahedron strut B31, where dashed lines show hidden edges of the strut. The strut B31 is an octahedron with an elongate portion of six substantially similar elongate faces and two end faces. The elongate faces B31$a$, B31$b$, B31$c$, B31$d$, B31$e$ & B31$f$ of the strut B31 define the outer surface of the strut's elongate and somewhat cylindrical surface. Each of the elongate faces B31$a$, B31$b$, B31$c$, B31$d$, B31$e$ & B31$f$ are isosceles triangles with a first internal angle, angle A, and a second internal angle, angle B, where angle B is greater than angle A. The strut B31 also has two end faces B3$f$ & B31$g$ that isosceles triangles that are substantially similar to one another, having a first internal angle, angle C, and a second internal angle, angle D, and where angle D is greater than angle C. When comparing the internal angles of the elongate faces B31$a$, B31$b$, B31$c$, B31$d$, B31$e$ & B31$f$ to the end faces B31$f$ & B31$g$, angle C is greater than angle A.

Figure 1J:
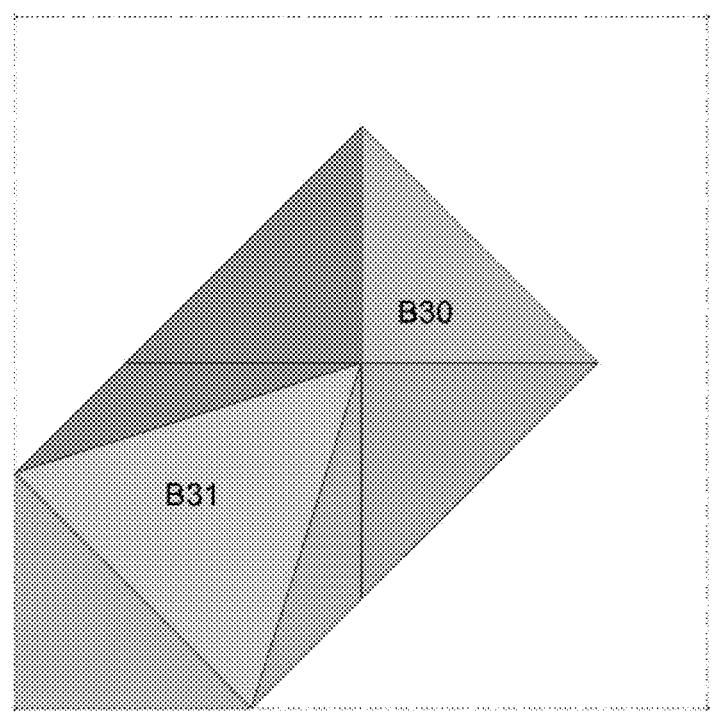
FIG. 1J is a side view of an example of a single node and single strut combination that could be used in a radial dodeca-rhombus unit cell.
Figure 1K:
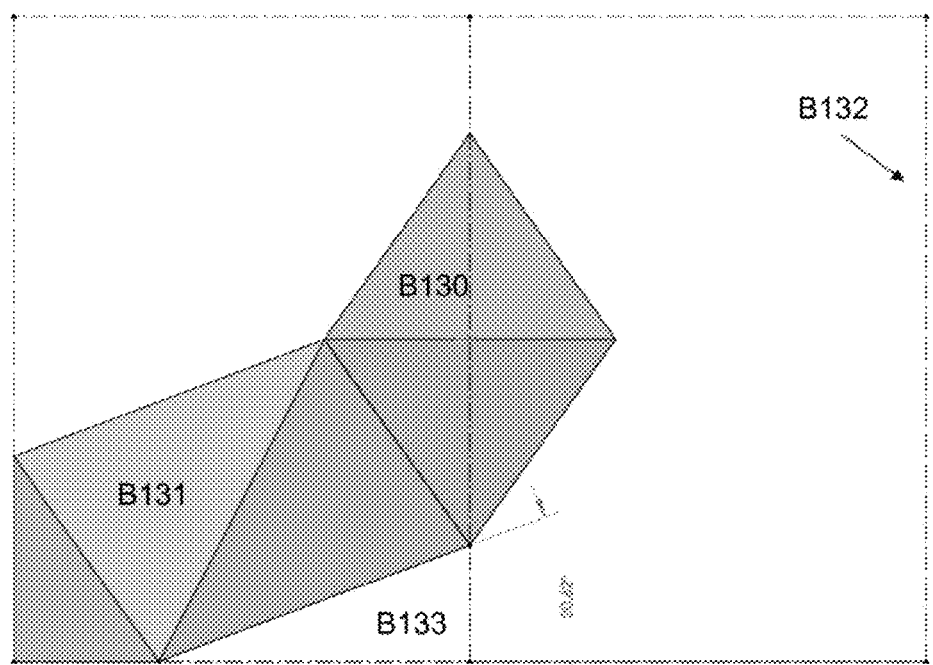
FIG. 1K is a side view of a single node and single strut combination configured for use in a lattice with an elastic modulus of approximately 3 GPa, viewed from the corner of the volume defining the bounds of the combination.
Figure 1L:
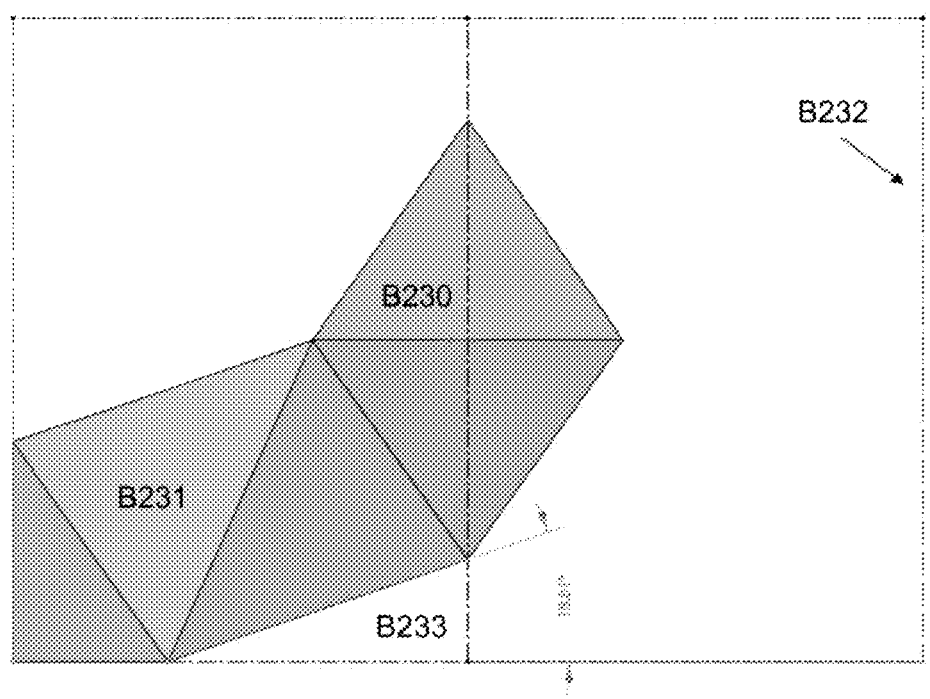
FIG. 1L is a side view of a single node and single strut combination configured for use in a lattice with an elastic modulus of approximately 4 GPa, viewed from the corner of the volume defining the bounds of the combination.
Figure 1M:
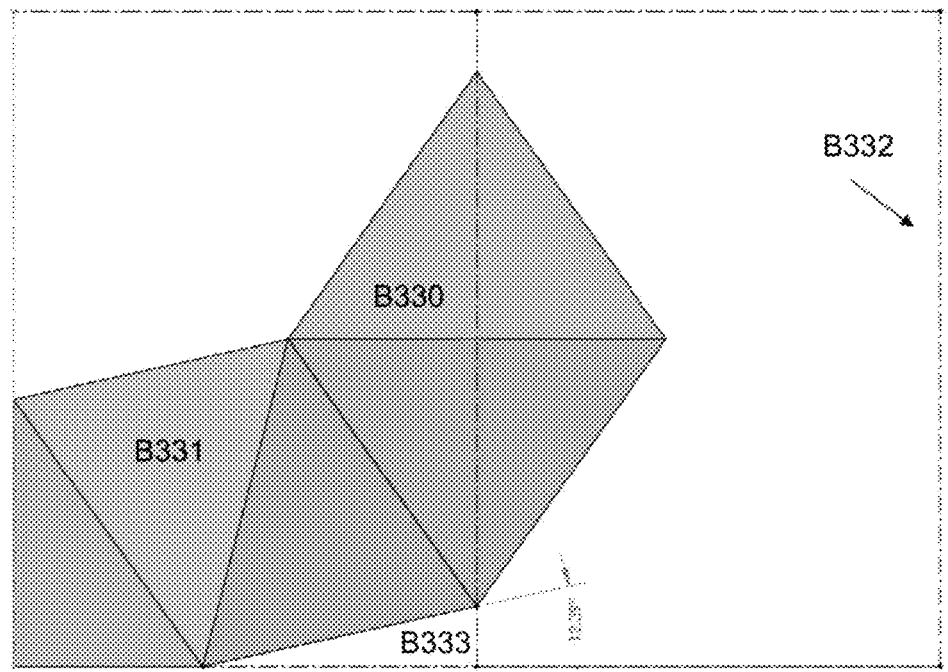
FIG. 1M is a side view of a single node and single strut combination configured for use in a lattice with an elastic modulus of approximately 10 GPa, viewed from the corner of the volume defining the bounds of the combination.

In FIG. 1J is a side view of the node B30 and strut B31 combination bounded by volume B32. In the side view, the height of the node B30 compared to the height of the cube B32 can be compared easily. In FIGS. 1K-1M are side views of node and strut combinations viewed from a corner of the volume rather than a wall or face, and where the combinations have been modified from FIGS. 1I-1J to change the volumetric density of the resulting unit cell. In FIG. 1K, the height of the node B130 has increased relative to the height of the volume B132. Since the distal end of the strut B131 is fixed by the location of a corner of the volume B132, the strut B131 must change its angle relative to its attached node face so that it becomes nonorthogonal. The node B130 and strut B131 combination, where the angle of the strut B131 from a horizontal plane is about 20.6 degrees, would be appropriate for a lattice structure with an elastic modulus of approximately 3 GPa.

In FIG. 1L, the height of the node B230 relative to the height of the cube B232 has been increased over the ratio of FIG. 1K to create a node B230 and strut B231 combination that would be appropriate for a lattice structure with an elastic modulus of approximately 4 GPa. As the height of the node B230 increases, the angle between the strut B231 and a horizontal plane decreases to about 18.8 degrees. As the height of the node B230 increases, the size of the node faces also increase so that the size of the strut B231 increases. While the distal end of the strut B231 is fixed to the corner of the volume B232, the size of the distal end increases to match the increased size of the node face to maintain a substantially even strut diameter along its length. As the node and strut increase in size, the volumetric density increases, as does the elastic modulus. In FIG. 1M, the height of the node B330 relative to the height of the volume B332 has been increased over the ratio of FIG. 1M to create a node B330 and strut B331 combination that would be appropriate for a lattice structure with an elastic modulus of approximately 10 GPa. In this configuration, the angle B333 between the strut B331 and a horizontal plane decreases to about 12.4 degrees and the volumetric density increases over the previous examples. The single node and strut examples can be copied and/or mirrored to create unit cells of appropriate sizes and characteristics. For instance, the angle between the strut and a horizontal plane could be increased to 25.8 degrees to render a lattice with a 12.3 percent volumetric density and an elastic modulus of about 300 MPa. While a single node and single strut were shown in the examples for clarity, multiple struts may be attached to each node to create an appropriate unit cell.

Adjacent struts extending from adjacent node faces on either the upper half or lower half of the node have an angle from the horizontal plane and a lateral separation angle defined by an angle between the strut directions of adjacent struts. In the MRDD and RDDR structures, adjacent struts have an external edge or face of the elongate portion extending closest to the relevant adjacent strut. The lateral separation angle, as used herein, generally refers to the angle between an external edge or face of the elongate portion of a strut extending closest to the relevant adjacent strut. In some embodiments, a lateral separation angle defined by a line extending between the center of the strut end faces or a line defined by the center of mass of the struts can be used in reference to a similar calculation for an adjacent strut.

Figure 1N:
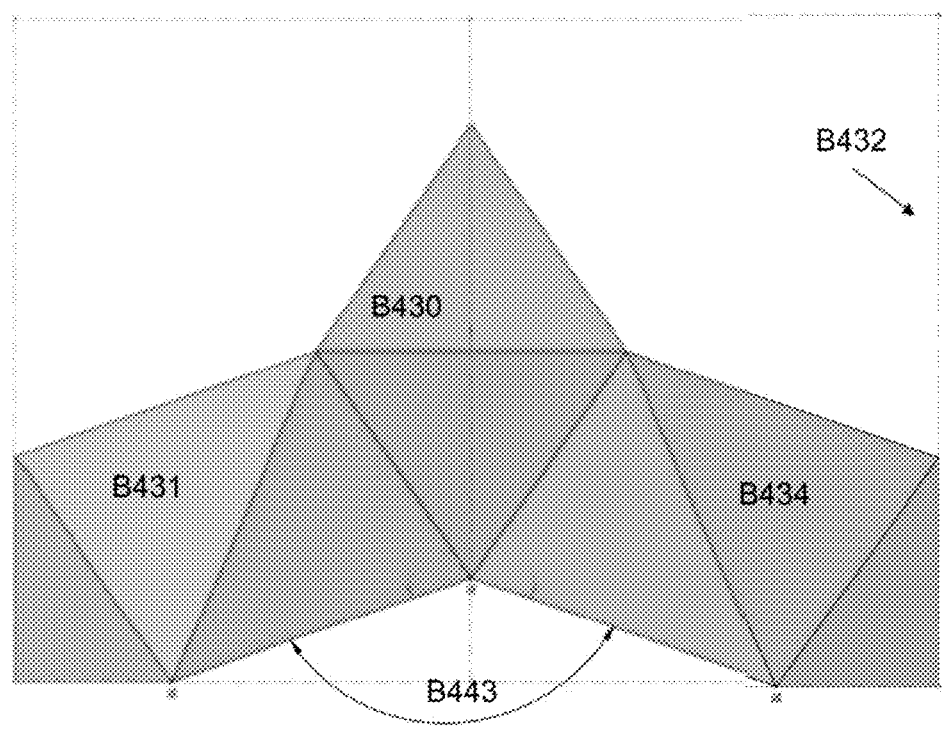
FIG. 1N is a side view of a single node and two adjacent struts viewed from the corner of the volume defining the bounds of the combination and the lateral separation angle.

The lateral separation angle is the angle between the nearest face or edge of a strut to an adjacent strut. The lateral separation angle can be measured as the smallest angle between the nearest edge of a strut to the nearest edge of an adjacent strut, in a plane containing both strut edges. The lateral separation angle can also be measured as the angle between the nearest face of a strut to the nearest face of an adjacent strut in a plane normal to the two strut faces. In embodiments without defined strut edges or strut faces, the lateral separation angle can be measured as an angle between the nearest portion of one strut to the nearest portion of an adjacent strut. For a unit cell in a cubic volume, as the strut angle from the horizontal plane decreases, the lateral separation angle approaches 90 degrees. For a unit cell in a cubic volume, as the strut angle from the horizontal plane increases, the lateral separation angle approaches 180 degrees. In some embodiments, it is preferable to have a lateral separation angle greater than 109.5 degrees. In some embodiments, it is preferable to have a lateral separation angle of less than 109.5 degrees. In some embodiments, it is preferable to have a lateral separation angle of between and including about 108 degrees to about 156 degrees. In some embodiments, it is more preferable to have a lateral separation angle of between and including 111 degrees to 156 degrees. In some embodiments, it is more preferable to have a lateral separation angle of between and including 108 degrees to 120 degrees. In some embodiments, it is most preferable to have a lateral separation angle of between and including about 111 degrees to 120 degrees. In some embodiments, it is more preferable to have a lateral separation angle of between and including 128 degrees to 156 degrees. In FIG. 1N is a side view, viewed from a corner of the cube B432, of a single node B430 with two adjacent struts B431 & B434 attached and where the lateral separation angle B443 is identified. When measured from the nearest edge of a strut to the nearest edge of an adjacent strut, the lateral separation angle B443 is about 116 degrees.

Figure 1P:
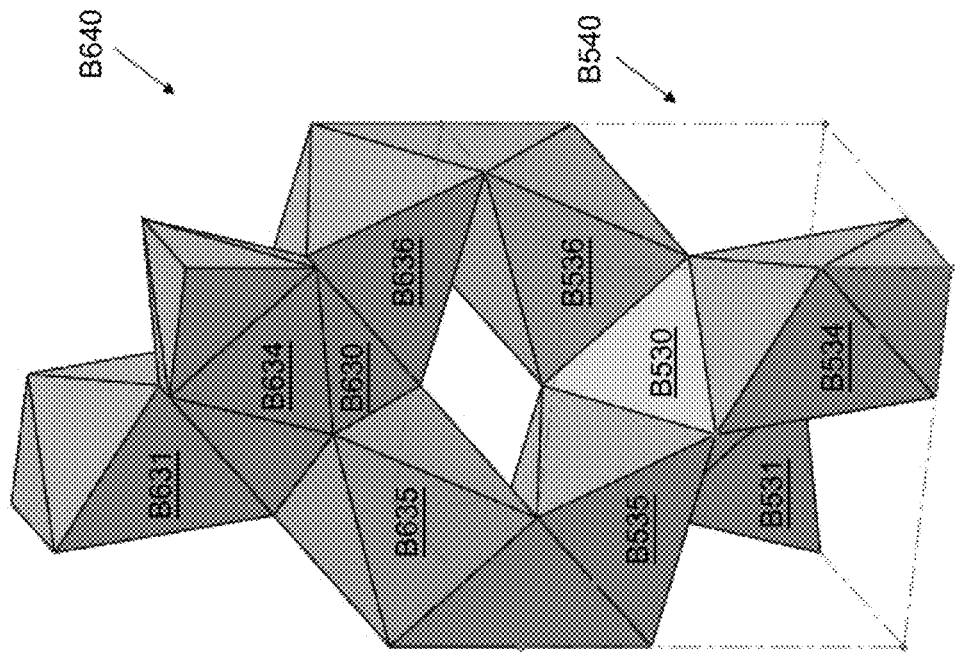
FIG. 1P is an isometric view of two sub-unit cells in a stacked formation where the upper sub-unit cell is inverted and fixed to the top of the lower sub-unit cell.
Figure 1O:
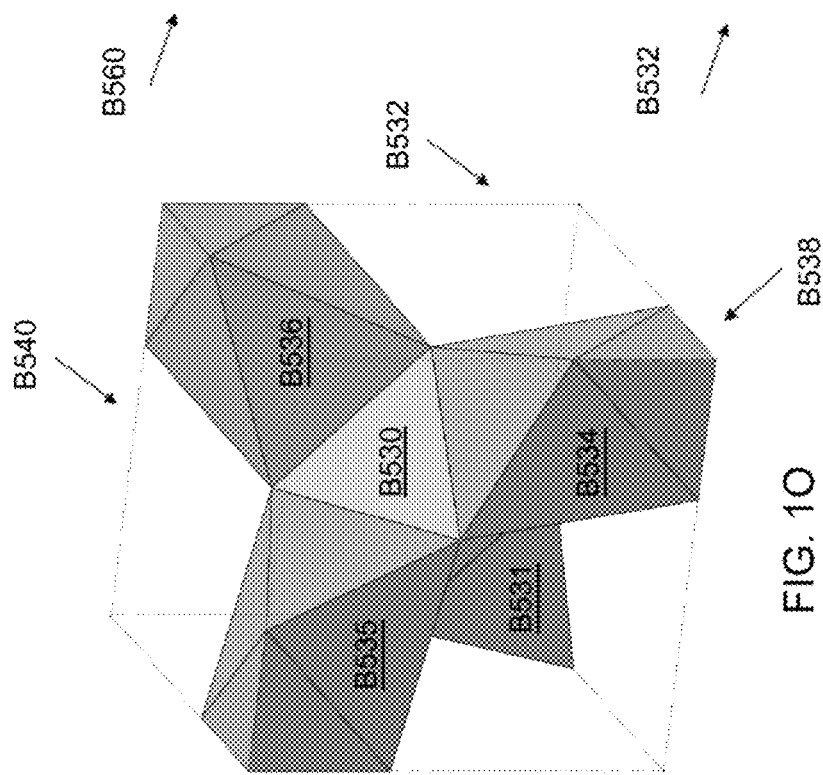
FIG. 1O is an isometric view of a sub-unit cell comprised of a single node and four struts.
Figure 1Q:
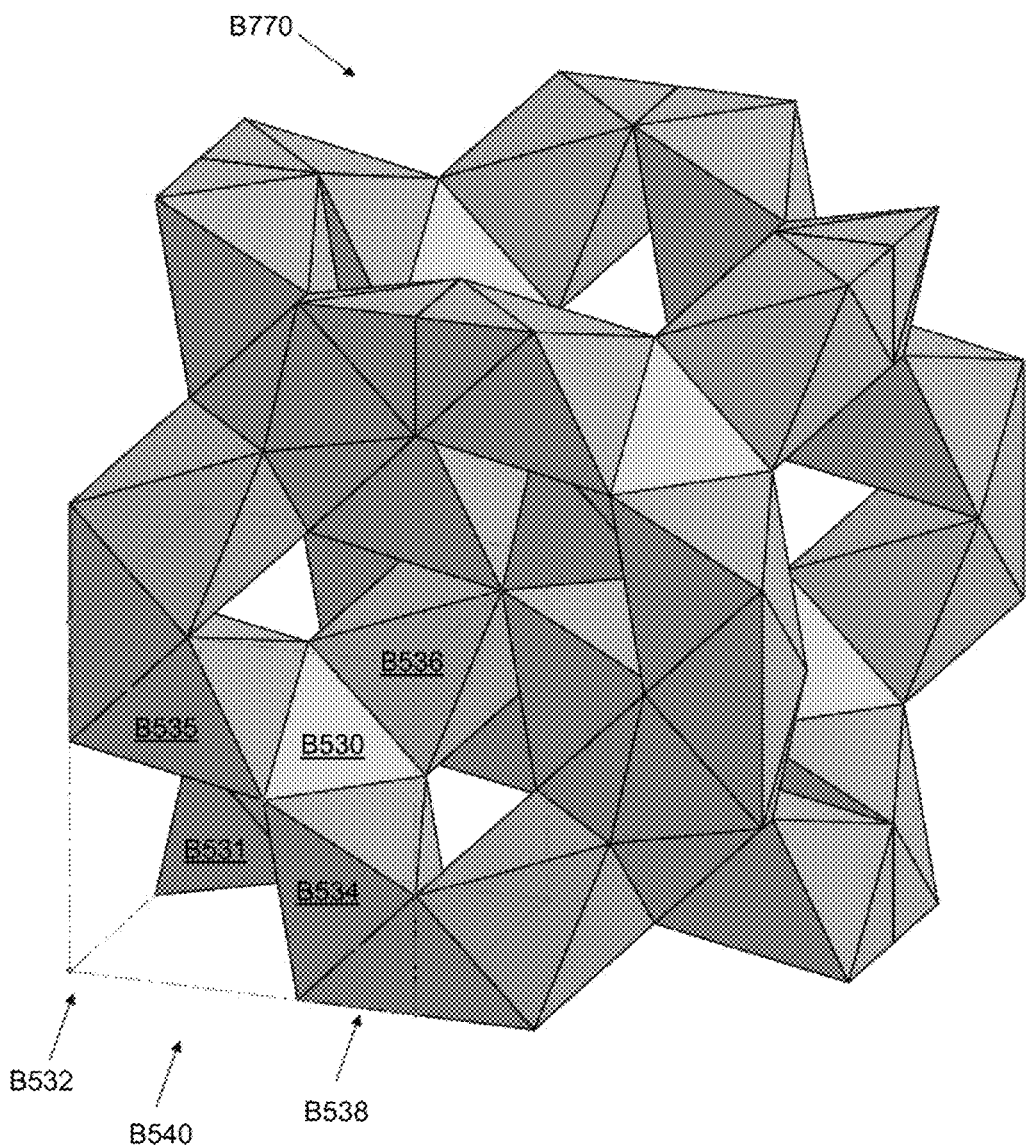
FIG. 1Q is an isometric view of eight sub-unit cells stacked together to form a single unit cell.

In some embodiments, a unit cell is built up from multiple sub-unit cells fixed together. In FIG. 1O is an isometric view of an exemplary sub-unit cell comprising a single node and four struts. In FIG. 1P is an isometric view of two sub-unit cells in a stacked formation where the upper sub-unit cell is inverted and fixed to the top of the lower sub-unit cell. In FIG. 1Q is an isometric view of eight sub-unit cells stacked together to form a single RDDR unit cell.

In FIG. 1O, the node B530 is a square bipyramid, oriented so that the two peaks face the top and bottom of a cubic volume B532. In some embodiments, the volume B532 can be a cuboid volume, a hexahedron volume, an amorphous volume or of a volume with one or more non-orthogonal sides. The peaks refer to the point where four upper faces meet and the point where four lower faces meet. The node B530 is oriented so that the horizontal vertices face the lateral sides of the cubic volume B532. The strut B531 is fixed to a lower face of the node B530 face on its proximate end and extends to the nearest corner of the cubic volume B532 at its distal end. The distal end of the strut B531 can remain fixed to the cubic volume B532 even if the node B530 changes in size to adjust the sub-unit cell properties.

On the lower face of the node B530 opposite the face which strut B531 is fixed, the proximate end of strut B534 is fixed to the node B530. The strut B534 extends to the nearest corner of cubic volume B532 at its distal end. The strut B535 is fixed on its proximate end to an upper node B530 face directed about 90 degrees laterally from the node B530 face fixed to strut B531. The strut B535 extends to the nearest corner of the cubic volume B532 at its distal end. On the upper face of the node B530 opposite the face which strut B535 is fixed, the proximate end of strut B536 is fixed to the node B530. The strut B536 extends to the nearest corner of the cubic volume B532 at its distal end.

In some embodiments, the struts B531 & B534-B536 are octahedrons with triangular faces. The strut face fixed to a node B530 face can be substantially the same size and orientation of the node B530 face. The strut face fixed to the nearest corner of the cube B532 can be substantially the same size as the strut face fixed to the node B530 and oriented on a substantially parallel plane. The remaining six faces can be six substantially similar isosceles triangles with a first internal angle and a second internal angle larger than said first internal angle. The six substantially similar isosceles triangles can be fixed along their long edges to an adjacent and inverted substantially similar isosceles triangle to form a generally cylindrical shape with triangular ends.

When forming a sub-unit cell B540, it can be beneficial to add an eighth node B538 to each corner of the cube B532 fixed to a strut B531 & B534-B536. When replicating the sub-unit cell B540, the eighth node B538 attached to each strut end is combined with eighth nodes from adjacent sub-unit cells to form nodes located between the struts of adjacent sub-unit cells.

In FIG. 1P is a first sub-unit cell B540 fixed to a second sub-unit cell B640 to form a quarter unit cell B560 used in some embodiments. The second sub-unit cell B640 comprises a square bipyramid node B630 is a square bipyramid, oriented so that the two peaks face the top and bottom of a cubic volume. The node B630 is oriented so that the horizontal vertices face the lateral sides of the cubic volume. The strut B635 is fixed to a lower face of the node B630 face on its proximate end and extends to the nearest corner of the cubic volume at its distal end. On the lower face of the node B630 opposite the face which strut B635 is fixed, the proximate end of strut B636 is fixed to the node B630. The strut B636 extends to the nearest corner of cubic volume at its distal end. The strut B634 is fixed on its proximate end to an upper node B630 face directed about 90 degrees laterally from the node B630 face fixed to strut B635. The strut B634 extends to the nearest corner of the cubic volume at its distal end. On the upper face of the node B630 opposite the face which strut B634 is fixed, the proximate end of strut B631 is fixed to the node B630. The strut B631 extends to the nearest corner of the cubic volume at its distal end.

The first sub-unit B540 is used as the datum point in the embodiment of FIG. 1P, however, it is appreciated that the second sub-unit cell B640 or another point could also be used as the datum point. Once the first sub-unit cell B540 is fixed in position, it is replicated so that the second sub-unit cell B640 is substantially similar to the first. The second sub-unit cell B640 is rotated about its central axis prior to being fixed on the top of the first unit-cell B540. In FIG. 1P, the second sub-unit cell B640 is inverted to achieve the proper rotation, however, other rotations about the central axis can achieve the same result. The first sub-unit cell B540 fixed to the second sub-unit cell B640 forms a quarter unit cell B560 that can be replicated and attached laterally to other quarter unit cells to form a full unit cell.

Alternatively, a full unit cell can be built up by fixing a first group of four substantially similar sub-unit cells together laterally to form a square, rectangle or quadrilateral when viewed from above. A second group of four substantially similar sub-unit cells rotated about their central axis can be fixed together laterally to also form a square, rectangle or quadrilateral when viewed from above. The second group of sub-unit cells can be rotated about their central axis prior to being fixed together laterally or inverted after being fixed together to achieve the same result. The second group is then fixed to the top of the first group to form a full unit cell.

In FIG. 1Q is an example of a full unit cell B770 formed by replicating the sub-unit cell B540 of FIG. 1O. The cube B532 defining the bounds of the sub-unit cell B540 is identified as well as the node B530 and struts B531 & B534-B536 for clarity. The full unit cell B770 of FIG. 1O can be formed using the methods described above or using variations within the inventive concept.

Each strut extending from the node, for a given unit cell, can be substantially the same length and angle from the horizontal plane, extending radially from the node. At the end of each strut, the strut is mirrored so that struts extending from adjacent node faces form a rhombus shaped opening. Because the struts can be non-orthogonal to the node faces, rhombuses of two shapes emerge. In this configuration, a first group of four rhombuses extend radially from the node oriented in vertical planes. The acute angles of the first group of rhombuses equal twice the strut angle from the horizontal plane and the obtuse angles equal 180 less the acute angles. Also in this configuration is a second group of eight rhombuses extending radially so that a portion of the second group of eight rhombuses fall within the lateral separation angle between adjacent struts defining the first group of four rhombuses. The acute angles of the second group of rhombuses can be about the same as the lateral separation angle between adjacent struts that define the first group of four rhombuses and the obtuse angles equal 180 less the acute angles. The characteristics of a scaffold may also be described by its surface area per volume. For a 1.0 mm×1.0 mm×1.0 mm solid cube, its surface area is 6.0 square mm. When a 1.0 cubic mm structure is comprised of a lattice structure rather than a 100 percent volumetric density material, the surface area per volume can increase significantly. In low volumetric density scaffolds, the surface area per volume increases as the volumetric density increases. In some embodiments, a scaffold with a volumetric density of 30.1 percent would have a surface area of 27.4 square mm per cubic mm. In some embodiments, if the volumetric density was decreased to 27.0 percent, the lattice would have a surface area of 26.0 square mm per cubic mm and if the volumetric density were decreased to 24.0 percent, the lattice would have a surface area of 24.6 square mm per cubic mm.

The MRDD and RDDR structures disclosed herein also have the advantage of an especially high modulus of elasticity for a given volumetric density. When used as a lattice or scaffold, an implant with an adequate modulus of elasticity and a low volumetric density can be achieved. A low volumetric density increases the volume of the implant available for bone ingrowth.

In Table 1, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in other embodiments. One advantage of the presently disclosed lattice structures is that the approximate actual elastic modulus is much closer to the design elastic modulus than has been previously achieved. During testing, one embodiment of a lattice was designed for a 4.0 GPa design elastic modulus. Under testing, the lattice had an actual elastic modulus of 3.1 GPa, achieving an actual elastic modulus within 77 percent of the design elastic modulus.

For each lattice design elastic modulus, a volumetric density, ratio of design elastic modulus to volumetric density, surface area in $mm^2$, ratio of surface area to volumetric density and ratio of surface area to lattice design elastic modulus is given.

TABLE 1

Table of example lattice structures based on lattice design elastic modulus in GPa

| Lattice Design Elastic Modulus (GPa) | Approx. Actual Elastic Modulus (GPa) | Volumetric Density (percent) | Ratio of Design Elastic Modulus to Volumetric Density | Surface Area (mm²) | Ratio of Surface Area to Volumetric Density | Ratio of Surface Area to Lattice Design Elastic Modulus |
|---|---|---|---|---|---|---|
| 0.3 | 0.233 | 18.5 | 1.6 | 22.5 | 121.5 | 74.9 |
| 3 | 2.33 | 29.9 | 10.0 | 27.5 | 92.2 | 9.2 |
| 4 | 3.10 | 33.4 | 12.0 | 28.8 | 86.4 | 7.2 |
| 5 | 3.88 | 36.4 | 13.8 | 29.9 | 82.2 | 6.0 |
| 6 | 4.65 | 38.8 | 15.5 | 30.7 | 79.1 | 5.1 |
| 7 | 5.43 | 40.8 | 17.2 | 31.3 | 76.9 | 4.5 |
| 8 | 6.20 | 42.1 | 19.0 | 31.8 | 75.4 | 4.0 |
| 9 | 6.98 | 43.2 | 20.8 | 32.1 | 74.3 | 4.0 |

In some of the embodiments disclosed herein, the required strut thickness can be calculated from the desired modulus of elasticity. Using the following equation, the strut thickness required to achieve a particular elastic modulus can be calculated for some MRDD and RDDR structures:

$$\text{Strut Thickness} = (-0.0035 \cdot (E^2)) + (0.0696 \cdot E) + 0.4603$$

In the above equation, "E" is the modulus of elasticity. The modulus of elasticity can be selected to determine the required strut thickness required to achieve that value or it can be calculated using a preselected strut thickness. The strut thickness is expressed in mm and represents the diameter of the strut. The strut thickness may be calculated using a preselected modulus of elasticity or selected to determine the modulus of elasticity for a preselected strut thickness.

In some embodiments, the unit cell can be elongated in one or more directions to provide a lattice with anisotropic properties. When a unit cell is elongated, it generally reduces the elastic modulus in a direction normal to the direction of the elongation. The elastic modulus in the direction of the elongation is increased. It is desirable to elongate cells in the direction normal to the direction of new bone growth contained within the interconnections, openings and central voids (if any). By elongating the cells in a direction normal to the desired direction of reduced elastic modulus, the shear strength in the direction of the elongation may be increased, providing a desirable set of qualities when designing a structural scaffold. Covarying the overall stiffness of the scaffold may augment or diminish this effect, allowing variation in one or more directions.

In some embodiments, the sub-unit cells may be designing by controlling the height of the node relative to the height of the volume that defines the sub-unit cell. Controlling the height of the node can impact the final characteristics and appearance of the lattice structure. In general, increasing the height of the node increases the strut thickness, increases the volumetric density, increases the strength and increases the elastic modulus of the resulting lattice. When increasing the height of the node, the width of the node can be held constant in some embodiments or varied in other embodiments.

In some embodiments, the sub-unit cells may be designing by controlling the volume of the node relative to the volume that defines the sub-unit cell. Controlling the volume of the node can impact the final characteristics and appearance of the lattice structure. In general, increasing the volume of the node increases the strut thickness, increases the volumetric density, increases the strength and increases the elastic modulus of the resulting lattice. When increasing the volume of the node, the width or height of the node could be held constant in some embodiments.

In Table 2, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in some embodiments. For each lattice design elastic modulus, a lattice approximate elastic modulus, a node height, a volumetric density, a node volume, a ratio of node height to volumetric density, a ratio of node height to lattice design elastic modulus and a ratio of volumetric density to node volume is given.

TABLE 2

Table of example lattice structures based on lattic design elastic modulus in GPa

| Lattice Design Elastic Modulus (GPa) | Lattice Approx. Actual Elastic Modulus (GPa) | Node Height (mm) | Volumetric Density (percent) | Node Volume (mm3) | Ratio of Node Height to Vol. Density | Ratio of Node Height to Lattice Design Elastic Modulus | Ratio of Vol. Density to Node Volume |
|---|---|---|---|---|---|---|---|
| 0.30 | 0.23 | 0.481 | 18.5 | 0.0185 | 2.60 | 1.60 | 9.98 |
| 3.00 | 2.33 | 0.638 | 29.9 | 0.0432 | 2.14 | 0.21 | 6.91 |
| 4.00 | 3.10 | 0.683 | 33.4 | 0.0530 | 2.05 | 0.17 | 6.29 |
| 5.00 | 3.88 | 0.721 | 36.4 | 0.0624 | 1.98 | 0.14 | 5.82 |
| 6.00 | 4.65 | 0.752 | 38.8 | 0.0709 | 1.94 | 0.13 | 5.48 |

TABLE 2-continued

Table of example lattice structures based on lattic design elastic modulus in GPa

| Lattice Design Elastic Modulus (GPa) | Lattice Approx. Actual Elastic Modulus (GPa) | Node Height (mm) | Volumetric Density (percent) | Node Volume (mm3) | Ratio of Node Height to Vol. Density | Ratio of Node Height to Lattice Design Elastic Modulus | Ratio of Vol. Density to Node Volume |
|---|---|---|---|---|---|---|---|
| 7.00 | 5.43 | 0.776 | 40.8 | 0.0779 | 1.90 | 0.11 | 5.23 |
| 8.00 | 6.20 | 0.793 | 42.1 | 0.0831 | 1.88 | 0.10 | 5.07 |
| 9.00 | 6.98 | 0.807 | 43.2 | 0.0877 | 1.87 | 0.09 | 4.93 |

Some embodiments of the disclosed lattice structures are particularly useful when provided within an elastic modulus range between an including 0.375 GPa to 4 GPa. Some embodiments, more preferably, include a lattice structure with an elastic modulus between and including 2.5 GPa to 4 GPa. Some embodiments include a lattice structure with a volumetric density between and including five percent to 40 percent. Some embodiments, more preferably, include a lattice structure with a volumetric density between and including 30 percent to 38 percent.

The lattice structures disclosed herein have particularly robust loading and fatigue characteristics for low volumetric density ranges and low elastic moduli ranges. Some embodiments of the lattice structures have a shear yield load and a compressive yield load between and including 300 to 15000 N in static and dynamic loading up to 5,000,000 cycles at 5 Hz. Some embodiments have a compressive shear strength and an axial load between and including 300 to 15000 N in static and dynamic loading up to 5,000,000 cycles at 5 Hz. Some embodiments have a shear strength and an axial load between and including 300 to 15000 N in static and dynamic loading up to 5,000,000 cycles at 5 Hz. Some embodiments have a torsional yield load up to 15 Nm.

In one example, the inventive lattice structure has a volumetric density of between and including 32 percent to 38 percent, an elastic modulus between and including 2.5 GPa to 4 GPa and a shear strength and an axial load between and including 300 to 15000 N in static and dynamic loading up to 5,000,000 cycles at 5 Hz. Some examples include a first set of substantially homogeneous openings with a width of about 200 m to 900 μm and a second set of substantially homogenous openings with a width of about 1 to 15 times the width of the first set of openings, where the number of openings in the second set are provided at a ratio of about 1:8 to 1:12 relative to the number of openings in the first set.

The disclosed structures can also have benefits when used in applications where osteointegration is not sought or undesirable. By including a growth inhibiting coating or skin on a structure, the lattice disclosed herein can be used to provide structural support without providing a scaffold for bone growth. This may be desirable when used in temporary implants or medical devices that are intended to be removed after a period of time.

Also disclosed herein is a method of designing a porous structure for use in medical implants. The method of design includes the steps of:

1. Modeling a sub-unit cell within a hexahedron volume of a preselected height, first width and second width, where the hexahedron volume comprises six hexahedron volume faces.

2. Modeling a node centrally located within the hexahedron volume, where the node comprises a square bipyramid with eight node faces and a square plane parallel to a face of said hexahedron volume, and the hexahedron volume further comprises eight corners, each defined by the intersection of three hexahedron volume faces.

3. Modeling a first strut fixed on its proximate end to a first node face and fixed on its distal end to a corner of the hexahedron volume nearest to the first node face.

4. Modeling a second strut fixed on its proximate end to a second node face, where the second node face is spaced about 180 degrees laterally from the first node face.

5. Modeling a third strut fixed on its proximate end to a third node face, where the third node face is spaced about 90 degrees laterally from the first node face.

6. Modeling a fourth strut fixed on its proximate end to a fourth node face, where the fourth node face is spaced about 180 degrees laterally from the third node face.

The method of designing a porous structure for use in medical implants may optionally include the step of modeling a unit cell by replicating the sub-unit cell and creating a first grouping of four sub-unit cells fixed to a second grouping of four sub-unit cells, where the first grouping comprises four substantially similar sub-unit cells arranged and fixed laterally in a quadrilateral when viewed from above, and where the second grouping comprises four substantially similar sub-unit cells inverted relative to the first grouping and fixed laterally in a quadrilateral when viewed from above.

When designing a porous structure for medical implants using the method disclosed herein, properties of the porous structure may be changed by changing a property of the sub-unit cell. Changes to the sub-unit cell that can change a property of the sub-unit cell include, but are not limited to, changing the height of the node, changing the volume of the node, changing a lateral dimension of the node, changing the height of the hexahedron volume, changing the first width of the hexahedron volume, or changing the second width of the hexahedron volume. In some embodiments, it is preferable to select a predetermined height of the hexahedron volume that is less than the first width or second width of the hexahedron volume.

The disclosed method of design can include identifying a reference plane defined by a hexahedron volume face and selecting a strut direction between 0 degrees to 90 degrees from the reference plane. The disclosed method of design can also include identifying a reference plane defined by a hexahedron volume face and selecting a strut direction between eight degrees to 30 degrees from the reference plane.

The lattice structure used in the disclosed method of design can include various structures, including but not limited to a rhombic dodecahedron, a modified rhombic dodecahedron or a radial dodeca-rhombus.

The method of designing a porous structure for use in medical implants can optionally further include the steps:

1. Identifying a principal axis defined by a line parallel to the height of the hexahedron volume.
2. Identifying a loading axis within 90 degrees of the principal axis.
3. Identifying a second loading axis oriented at an angle offset from the loading axis.
4. Configuring the implant to provide an elastic modulus along the loading axis of between and including 0.3 GPa to 12 GPa and an elastic modulus along the second loading axis of between and including 2 GPa to 25 GPa, where the elastic modulus along the loading axis is less than the elastic modulus along the second loading axis.

The present invention disclosed herein also includes a biocompatible lattice structure with anisotropic properties (hereinafter "anisotropic lattice") and a method of use. Only the preferred embodiments are shown herein and it is understood that the use of other unit cell structures would be within the inventive concept expressed herein.

In general, the elastic modulus of a lattice structure and the volumetric density of that structure are related. Decreasing the volumetric density decreases the elastic modulus and vice versa. When a substantially isotropic lattice is used as a structural scaffold, the resulting implant may require a design compromise in at least one direction. For example, a structural scaffold, if used in the spine, must be capable of resisting shear in the anterior-posterior direction and torsion around the superior-inferior axis while resisting compression in the superior to inferior direction. If isotropic, a structural scaffold would have substantially identical properties in all directions, requiring the structural scaffold to be designed based on the highest forces expected in all directions. The anisotropic lattice structures of the present invention are preferably comprised of multiple unit cells that can be substantially the same or different for the relevant portion of the structure. The relevant portion of a structure is the portion of a structure where specific properties are required. The relevant portion may include many adjacent unit cells or a single unit cell, depending on the specific properties required.

In the disclosure herein, the struts that define the unit cells and anisotropic lattice structures can be of substantially the same diameter for a single unit cell or multiple unit cells. Varying the diameter of the struts can allow the mechanical properties of the resulting lattice to be changed without changing the overall shape of the unit cells. While the struts are sometimes described as substantially the same diameter, it is understood that manufacturing tolerances may not allow struts of substantially the same diameter in certain applications. In particular, when the unit cell is smaller, the strut diameter is more difficult to control. The concepts of the present invention could also work in an anisotropic lattice with struts of different diameters or variations in the strut diameter.

The unit cells of the anisotropic lattice structures are described herein as shortened or elongated in one or more directions. Because the size of each unit cell can be scaled to suit a particular material or targeted mechanical properties, a unit cell may be shortened or elongated then scaled to the appropriate size.

Figure 2:
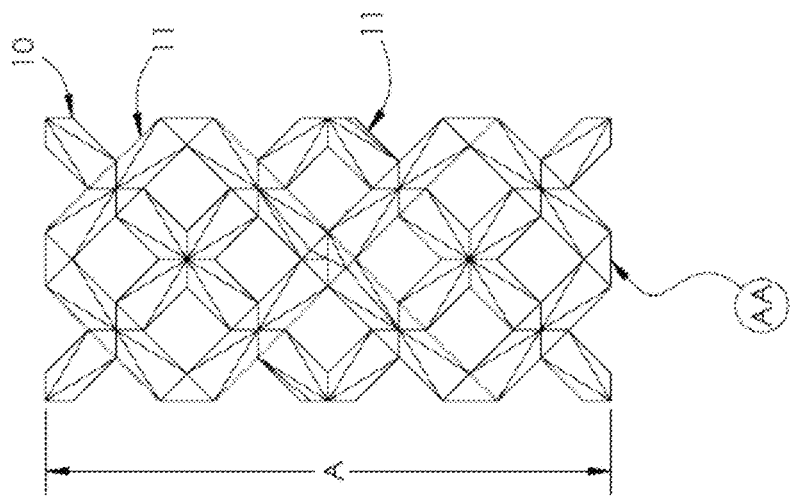
FIG. 2 is a front view of a modified rhombic dodecahedron lattice.
Figure 1R:
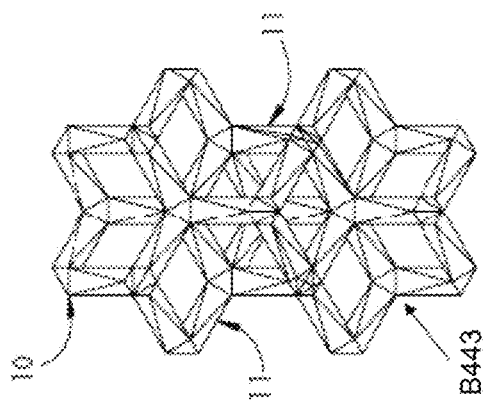
FIG. 1R is an isometric view of a modified rhombic dodecahedron lattice.
Figure 3:
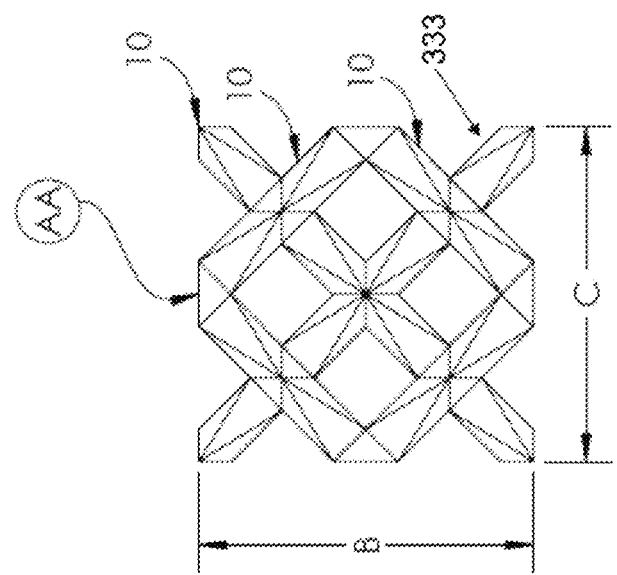
FIG. 3 is a bottom view of a modified rhombic dodecahedron lattice.

FIGS. 1-3 show a repeatable unit cell structure of a modified rhombic dodecahedron lattice 10 where the shape of the unit cells is defined by struts 11. The example shown is of a single complete MRDD unit cell, which includes additional struts extending outward that show the interfacing geometry of adjacent unit cells.

In FIG. 1-3 is an isometric view of the MRDD lattice 10. In FIG. 2 is a front view and in FIG. 3 is a bottom view of the MRDD lattice 10. The side views and back view are substantially the same as the front view. The top view is substantially the same as the bottom view. In the MRDD lattice, each unit cell is a modified rhombic dodecahedron with twelve sides in the shape of rhombuses. Because the MRDD unit cell shown is an open cell structure, each side of the MRDD is defined by four struts 11 that form a rhombus in a flat plane.

The MRDD lattice 10 in this example is substantially isotropic, where each of the twelve sides of the unit cell are substantially the same size and shape. The struts 11 that form the sides are also a substantially equal length and thickness. As used herein, the term "substantially" includes values up to 10 percent above or below the referenced value. In FIG. 2, the length of the section of MRDD lattice 10 in the z direction is defined by height A. In the section of MRDD lattice 10 shown in FIG. 2, the height A is equal to the height of two unit cells. In FIG. 3, the length of the section of MRDD lattice 10 in the x direction is defined by width B and the length of the section of MRDD lattice 10 in the y direction is defined by width C. In the section of MRDD lattice shown in FIG. 3, width B and width C are equal to the height of a single unit cell. Because the height A is equal to the height of two unit cells, width B and width C are equal to one half of height A. Point AA is identified on FIGS. 2 & 3 for additional clarity.

The MRDD lattice 10 has largely isotropic properties when compressed in the direction of the x, y and z axes. When the MRDD lattice 10 is used in an interbody spinal fusion implant, the mechanical properties provided by the lattice are substantially the same in the superior to inferior direction, the anterior to posterior direction and the lateral direction. When used herein for direction or orientation, the superior to inferior direction, the anterior to posterior direction and the lateral directions correspond to the z, x and y directions, respectively. These specific directional references are exemplary and used to the example orientations described herein.

When using a lattice as a structural support in an interbody spinal fusion implant, the lattice must have sufficient torsional and shear strength on the transverse plane, a generally horizontal plane defined by the anterior to posterior and lateral directions. When an MRDD unit cell is designed to have sufficient torsional and shear strength on the transverse plane, the elastic modulus in the superior to inferior direction is often higher than optimal. A high elastic modulus in the superior to inferior direction can cause stress shielding of new bone growth, resulting in slow and weak new bone growth. Additionally, a lattice of the same volumetric density may maintain thicker struts by the mechanism of increasing the unit cell size and thus achieve greater resistance to fatigue in all directions and a reduced stiffness in one direction.

When the elastic modulus of an interbody spinal fusion implant in the superior to inferior direction is high, the interbody implant takes the physiological load as the patient moves, rather than the new bone growth. In accordance with Wolff's law, new bone growth that is shielded from stress is weaker than bone that is subject to normal mechanical stimulation. Because an isotropic lattice has substantially identical mechanical properties along the x, y and z axes, it is not as ideal for use as a load bearing scaffold for bone growth as an anisotropic lattice.

Figure 4:
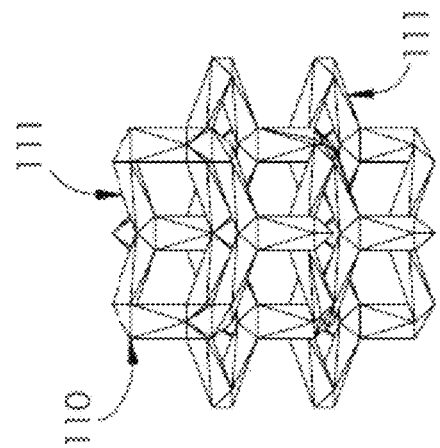
FIG. 4 is an isometric view of a first exemplary embodiment of an anisotropic lattice structure, showing an elongated modified rhombic dodecahedron lattice.
Figure 6:
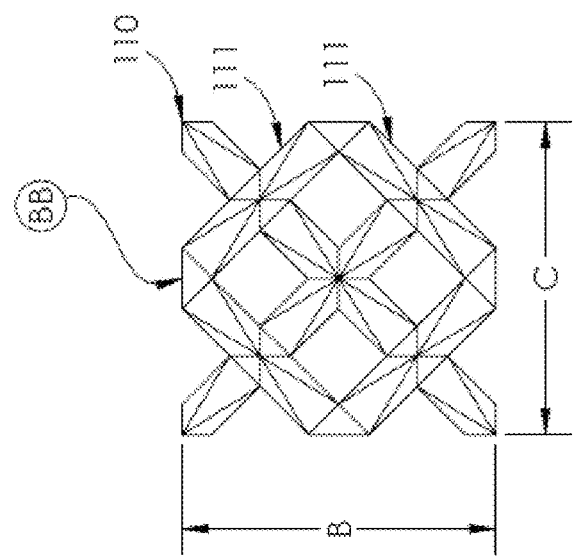
FIG. 6 is a is a bottom view of a first exemplary embodiment of an anisotropic lattice structure, showing an elongated modified rhombic dodecahedron lattice.
Figure 5:
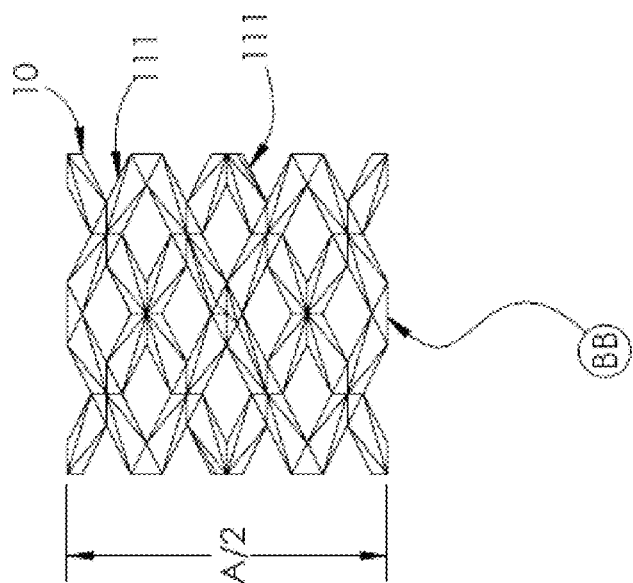
FIG. 5 is a front view of a first exemplary embodiment of an anisotropic lattice structure, showing an elongated modified rhombic dodecahedron lattice.

FIGS. 4-6 show a repeatable unit cell structure of a first embodiment of the present invention. The first embodiment is an elongated MRDD lattice 110 where the shape of the unit cells is defined by struts 111. The first embodiment is a single complete elongated RDD cell with additional struts extending outward that represent portions of a repeating structure. In FIG. 4 is an isometric view, in FIG. 5 is a front view and in FIG. 6 is a bottom view of the elongated MRDD lattice 110. The side views and back view are substantially the same as the front view. The top view is substantially the same as the bottom view.

In the elongated MRDD lattice 110, each unit cell is the intersection of elongated modified rhombic dodecahedrons defined by twelve sides in the shape of rhombuses. Because the elongated MRDD lattice 110 has an open cell structure, each side of the unit cell is defined by four struts 111 that form a rhombus in a flat plane. The elongated MRDD lattice 110 is elongated in the x and y directions so that the width of a single cell is equal to width B and width C in the x and y directions, respectively, and the height of two cells is equal to half of height A. In other words, the width of a single cell in the x or y direction is twice the height of a single cell in the z direction in this embodiment. Point BB is identified on FIGS. 5 & 6 for additional clarity.

To achieve an MRDD cell structure that is wider than tall, the length of struts in the cell are preferably changed, altering the dimension of the cell. This allows for preferential variation of a cell dimension in any direction. In the example, struts are shortened in the vertical direction, reducing the cell height and stiffness in that cell direction.

The elongated MRDD lattice 110 has anisotropic properties that make it particularly useful as a scaffold for bone growth. By creating a unit cell that is wider than tall, the resulting scaffold has a lower elastic modulus in the vertical direction than in the horizontal direction. If used in the spine, the resulting lattice would allow greater compression in the superior to inferior direction, while maintaining a high shear strength in the anterior to posterior and lateral directions. The reduced elastic modulus in the superior to inferior direction reduces stress shielding and promotes fusion.

Figure 8:
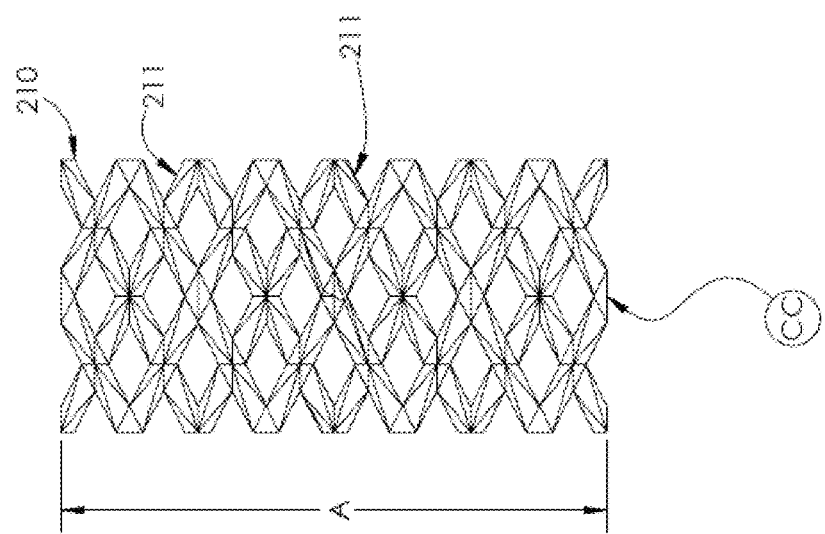
FIG. 8 is a front view of a second exemplary embodiment of an anisotropic lattice structure, showing an alternate elongated modified rhombic dodecahedron lattice.
Figure 7:
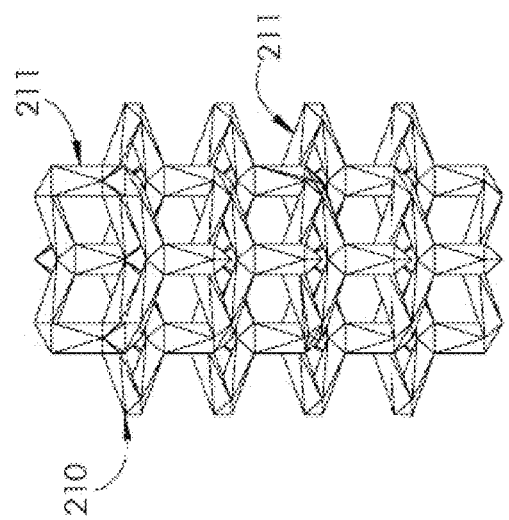
FIG. 7 is an isometric view of a second exemplary embodiment of an anisotropic lattice structure, showing an alternate elongated modified rhombic dodecahedron lattice.

FIGS. 7-9 show a repeatable unit cell structure of a second embodiment of the present invention. The second embodiment is an elongated MRDD lattice 210 where the shape of the unit cells is defined by struts 211. The second embodiment is a stack of three complete elongated MRDD unit cells with additional struts extending outward that represent portions of a repeating structure. In FIG. 7 is an isometric view, in FIG. 8 is a front view and in FIG. 9 is a bottom view of the elongated MRDD lattice 210. The side views and back view are substantially the same as the front view. The top view is substantially the same as the bottom view.

In the elongated MRDD lattice 210, each unit cell is the intersection of elongated modified rhombic dodecahedrons defined by twelve sides in the shape of rhombuses. Because the elongated MRDD lattice 210 has an open cell structure, each side of the unit cell is defined by four struts 211 that form a rhombus in a flat plane. The elongated MRDD lattice 210 is elongated in the x and y directions so that the width of a single cell in the x direction is equal to width B, the width of a single cell in the y direction is equal to width C, and the height of two cells in the z direction is equal to half of height A. In other words, the width of a single cell in the x and y directions is twice the height of a single cell in the z direction in this embodiment. Point CC is identified on FIGS. 8 & 9 for additional clarity.

While the exemplary embodiments of the anisotropic lattice are elongated by the same amount in the x and y directions relative to the z direction, other ratios of width to height are within the inventive scope of the present invention. Depending on the specific application where the lattice structure is needed, the width in the x or y direction can be any value other than the height in the z direction of a unit cell. While the description of the present invention defines the elongation of the unit cell relative to the x, y and z directions, the lattice structure can be rotated or oriented to create a lattice with the proper mechanical properties for a specific application. For instance, the unit cells of the lattice could have a height in the z direction that is greater than the width in the x and y directions for applications where compression along the vertical axis is undesirable. The lattice structure may also be rotated to design a lattice for specific mechanical properties in other than the horizontal and vertical directions. It is also possible to obtain different mechanical properties in directions that are not 90 degrees apart.

The exemplary embodiments described herein use a width B that is equal to width C, however, it is appreciated that it could be desirable to create a unit cell with a width B that is not equal to width C. By changing the width of the unit cell in only one direction, different mechanical properties may be achieved along that axis.

While the x, y and z axis have been used herein to describe the present invention, the anisotropic lattice described herein can be adapted to the orientation or orientations needed for a particular purpose. For instance, the principal axis line does not need to be a straight or vertical line following the z axis. In one example, the principal axis line follows the lordosis of the spine. In another example, the lattice structure varies throughout to achieve an implant whose principle axis follows the lordosis of the spine. The dimensions of each unit cell can be identical for a relevant portion at one extreme or they can all be different at the other extreme, depending on the mechanical properties desired. The dimensions of unit cells can be organized in layers one or more unit cell in height and one or more unit cell in width. Unit cells within a certain layer can share dimensional properties and therefore mechanical properties.

The shape of the unit cells can also be adjusted to increase the torsional and shear strength of the lattice in the x and y directions. The torsional and shear strength can be adjusted by changing the dimensions of all unit cells or preferentially by only changing the dimensions of the cells in particular portions of the lattice structure. In one example, the unit cells are changed only near the top or bottom of the lattice structure.

The anisotropic lattice structures disclosed herein can be produced from a range of materials and processes. When used as a bone scaffold it is often desirable for the anisotropic lattice to be made of a biocompatible material that allows for bone attachment, either to the material directly or through the application of a bioactive surface treatment. In one example, the anisotropic lattice is comprised of an implantable metal.

In another exemplary embodiment, the anisotropic lattice is comprised of an implantable metal with an elastic modulus along the z axis in the range of bone. In one example, the elastic modulus in the z direction is from 0.3 to 2.0 GPa and the elastic modulus in the x and y directions is from 2.0 to 25.0 GPa. In another example, the elastic modulus in the z direction is from 2.0 to 4.0 GPa and the elastic modulus in the x and y directions is from 4.0 to 25.0 GPa. In another example, the elastic modulus in the z direction is from 4.0 to 12.0 GPa and the elastic modulus in the x and y directions is from 12.0 to 25.0 GPa. In another example, the elastic modulus in the z direction is from 0.3 to 12.0 GPa and the elastic modulus in the x and y directions is from 10.0 to 25.0

GPa. In another exemplary embodiment, the anisotropic lattice is comprised of titanium or a titanium alloy with an elastic modulus along the z axis in the range of bone. In one example, the elastic modulus in the z direction is from 0.3 to 2.0 GPa and the elastic modulus in the x and y directions is from 2.0 to 25.0 GPa. In another example, the elastic modulus in the z direction is from 2.0 to 4.0 GPa and the elastic modulus in the x and y directions is from 4.0 to 25.0 GPa. In another example, the elastic modulus in the z direction is from 4.0 to 12.0 GPa and the elastic modulus in the x and y directions is from 12.0 to 25.0 GPa. In another example, the elastic modulus in the z direction is from 0.3 to 12.0 GPa and the elastic modulus in the x and y directions is from 10.0 to 25.0 GPa.

In some embodiments, the elastic modulus of a lattice can be referenced based on a line bisecting an internal angle of a vertex of a rhombic opening. In one embodiment, the elastic modulus in a first direction of loading, where the first direction is perpendicular to the line bisecting an internal angle of a vertex of a rhombic opening, is between and including 0.3 GPa and 12.0 GPa, the elastic modulus in a second direction of loading that is offset from the first direction is between and including 2.0 GPa to 25.0 GPa and where the elastic modulus in the first direction is less than the elastic modulus in the second direction.

The anisotropic lattice structures disclosed herein can also be described as a porous structure for medical implants comprising repeating unit cells within a defined volume with a length along a principal axis, an x axis normal to the principal axis and a y axis normal to the x axis, a loading direction within 90 degrees of the principal axis and where the elastic modulus of the structure is lower along the loading direction than along the x axis. In some embodiments, the porous structure can have an elastic modulus that is lower along the loading direction than along the y axis. The lattice structure can also be provided, in some embodiments, as a plurality of layers of homogenous repeating unit cells fixed along the x axis and y axis where at least one layer has a higher modulus of elasticity along the loading direction than an adjacent layer. In some embodiments with multiple layers of repeating unit cells, the loading direction of each layer can follow the lordosis of the spine. In some embodiments with multiple layers of repeating unit cells, the direction of each layer can follow the curvature of the device. In some embodiments with multiple layers of repeating unit cells, the direction of each layer can follow the curvature of the surrounding tissue or bone structures. As noted previously, some embodiments of the lattice structure can comprise a rhombic dodecahedron structure, the modified rhombic dodecahedron structure or a radial dodecarhombic structure.

Some embodiments of the anisotropic structures disclosed herein can have an elastic modulus in a loading direction between and including 0.3 GPa to 12 GPa and an elastic modulus along the x axis between and including 2 GPa to 25 GPa, where the elastic modulus in the loading direction is less than the elastic modulus along the x axis. In some embodiments, the length along the principal axis is less than the length along the x axis. In some embodiments, the length along the principal axis is less than the length along the y axis. In other embodiments, the length along the x axis is about the same as the length along the y axis.

In some embodiments optimized for promoting bone in-growth, the principal axis can be aligned with the desired direction of bone growth, where the desired direction of bone growth is the direction of bone growth away from a bony structure. Some embodiments optimized to promote bone in-growth can have a volumetric density between and including 5 percent to 40 percent and more preferably a volumetric density of between and including 30 percent to 38 percent. When optimized for bone in-growth, it is preferable for some embodiments of the lattice to have an elastic modulus in one direction of between and including 0.375 GPa to 4 GPa. It can also be beneficial for the lattice structures to have a compressive shear strength and an axial load between and including 300 to 15000 N in static and dynamic loading up to 5,000,000 cycles at 5 Hz and a torsional yield load of up to 15 Nm.

The lattice structures disclosed herein, in some examples, can be included in medical implants when the lattice structure is configured to promote bone in-growth, where the lattice structure is configured for implantation in an area between at least two bony structures where bone growth is desired, where bony structures are a portion of a patient's tissue near or abutting the bone fusion implant when implanted, where a principal axis intersects both of the two bony structures, where a loading axis is within 90 degrees of the principal axis, where the lattice structure is configured to provide the sole mechanical spacing between the two bony structures, where a second loading axis intersects the loading axis; and where the lattice structure has a lower modulus of elasticity along the loading axis than along the second loading axis.

While bone attachment is desirable when the elongated lattice of the present invention is used as a bone growth scaffold, the present invention may be used for mechanical support within the body without bone ingrowth. In one example, the anisotropic lattice is comprised of polyether ether ketone (hereinafter "PEEK"), a commonly used polymer in medical devices that does not allow for bone attachment without a surface treatment. It would be beneficial to use PEEK for temporary implants or for implants that may need to be removed in the future. Manufacturing processes that can be used to produce the present invention in PEEK include, but are not limited to, 3D printing and extrusion printing.

While an elongated MRDD has been shown herein as the unit cell structure of the preferred embodiments, there are many types of unit cell structures that can be elongated in one or more directions. Possible unit cell that are appropriate include, but are not limited to, rhombic dodecahedron, diamond, dodecahedron, square, pentagonal, hexagonal and octagonal. An anisotropic lattice may be achieved with a unit cell using as few as four sides. The changes in width relative to the height of a unit cell necessary to achieve the desired mechanical properties are different for different unit cell shapes and materials.

The anisotropic lattice is preferably created using a repeating elongated MRDD unit cell because of the unique strength to weight ratio of the structure. Due to the strength to weight characteristics of the elongated MRDD unit cell, the resulting anisotropic lattice can be produced with a lower volumetric density for a given stiffness. The lower volumetric density allows for a greater amount of volume for bone ingrowth and can result in stronger new bone growth. In some embodiments, the anisotropic lattice is preferably created using a repeating elongated RDDR unit cell, also for its unique strength to weight characteristics.

The embodiments of the anisotropic lattice disclosed herein can be used in a method of reducing stress shielding of new bone growth in spinal fusion procedures. In spinal fusion procedures, the damaged or diseased spinal disc is removed and replaced with an interbody device that provides mechanical spacing between the endplates of the adjacent vertebrae and a path for new bone to grow between the adjacent vertebrae. Over time, new bone growth from the adjacent vertebrae eventually grow together and fuse into a single bone.

When an interbody device has excess rigidity or an unnecessarily high elastic modulus, it tends to take the strain when the patient moves, rather than the new bone growth. When this occurs, the new bone growth is shielded from stress and in accordance with Wolff's law, the new bone growth is weaker than that it would have been if subject to normal physiological stresses. In the spine, controlling the elastic modulus in the superior to inferior direction or in the direction defined by the lordosis of the spine is theorized to be important to the loading of new bone growth.

The present method of reducing stress shielding involves creating an interbody device that provides some or all of the mechanical spacing between the endplates of the adjacent vertebrae with an anisotropic lattice comprised of one or more unit cells disclosed herein. By repeating one or more of the unit cells disclosed herein, the resulting interbody device preferably has a lower elastic modulus in the superior to inferior direction or the direction defined by the lordosis of the spine than in the anterior to posterior or lateral directions. A spinal fusion device using cells elongated in the anterior to posterior or lateral directions allows a reduced elastic modulus in the superior to inferior direction or the direction defined by the lordosis of the spine without significantly changing the torsional and shear strength in other directions.

A reduced elastic modulus in the superior to inferior direction or the direction defined by the lordosis of the spine is desirable because it allows the endplates of the adjacent vertebrae to move in a limited amount relative to one another, placing stress on the new bone growth. The strength of the interbody must remain high enough to provide adequate stability, but low enough to share loading, thereby preventing stress shielding in the new bone growth.

Also disclosed is a method of reducing stress shielding in all implants, steps comprising:
1. Providing an implant comprised at least in part of a lattice structure, where the lattice structure comprises repeating unit cells configured to allow tissue in-growth.
2. Defining an implant space near or abutting two areas of tissue.
3. Defining a principal axis that intersects both of the two areas of tissue.
4. Defining a loading axis within 90 degrees of the principal axis.
5. Configuring the implant to provide the sole mechanical spacing between the two areas of tissue in at least one plane intersecting the loading axis; and
6. Configuring the repeating unit cells so that they are shorter along the loading axis than in any other direction.

In the above method, the repeating unit cells can use various lattice structures, including but not limited to a rhombic dodecahedron, a modified rhombic dodecahedron or a radial dodeca-rhombus. The implant is preferably configured to be implanted near or abutting an area of tissue. The areas of tissue can be various types of tissue, including but not limited to, fibrous tissue or bony tissue. Areas of tissue can be as small as a single cell and can be part of a continuous surface or tissue or bone. The plane intersecting the loading axis can be a flat plane, but is not necessarily so. The intersecting plane can be, for example, a curved plane. The intersecting plane preferable defines a continuous layer between the two areas of tissue where the lattice structure provides the sole mechanical spacing between the areas of tissue.

The above method of reducing stress shielding can include the steps of:
1. Identifying a second loading axis oriented at an angle offset from the loading axis.
2. Configuring the implant to provide an elastic modulus along the loading axis of between and including 0.3 GPa to 12 GPa and an elastic modulus along the second loading axis of between and including 2 GPa to 25 GPa, where the elastic modulus along the loading axis is less than the elastic modulus along the second loading axis.

In some aspects, what has been described is a biocompatible lattice structure, capable of design with anisotropic properties and a method of reducing stress shielding of new bone growth in spinal fusion procedures. While this disclosure describes the use of a lattice or an anisotropic lattice as a bone scaffold, all or part of the invention is capable of being used in other applications. In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

The invention claimed is:

1. A porous lattice structure for medical implants, the porous lattice structure comprising:
a repeating unit cell, the repeating unit cell comprising a plurality of sub-unit cells;
wherein:
each of the plurality of sub-unit cells comprise six faces and is defined by a node centrally located within a cuboid volume;
the node comprises a square bipyramid with eight node faces and a square plane parallel to a face of the cuboid volume; and
each of the plurality of sub-unit cells comprises a first strut fixed to one of the eight node faces of the node defining that sub-unit cell.

2. The porous lattice structure of claim 1, wherein the node further comprises six vertices and the node is oriented so that each of the six vertices is positioned at their closest possible location to each of the six faces of the cuboid volume.

3. The porous lattice structure of claim 1, wherein:
the first strut is elongate;
the cuboid volume further comprises eight corners, each defined by an intersection of three cuboid volume faces; and
the first strut is fixed to a first node face on its proximate end and fixed to a corner of cuboid volume nearest to the first node face on its distal end.

4. The porous lattice structure of claim 3, wherein a strut direction of the first strut intersects a center of the node and a corner of the cuboid volume.

5. The porous lattice structure of claim 3, wherein the strut direction of the first strut intersects a corner of the cuboid volume.

6. The porous lattice structure of claim 3, wherein at least one of cuboid volume faces defines a reference plane and the strut direction of the first strut is between 0 degrees to 90 degrees from the reference plane.

7. The porous lattice structure of claim 3, wherein at least one of a cuboid volume face defines a reference plane and the strut direction of the first strut is between and including 8 degrees to 30 degrees from the reference plane.

8. The porous lattice structure of claim 1, wherein the node comprises a volumetric density of 100 percent.

9. The porous lattice structure of claim 1, wherein:
the first strut comprises an octahedron comprising an elongate portion of six substantially similar elongate faces and two end faces;
the elongate faces are isosceles triangles having a first internal angle, angle A, and a second internal angle, angle B, angle B being greater than angle A;
the two end faces are substantially similar isosceles triangles with a first internal angle, angle C, and a second internal angle, angle D, angle D being greater than angle C.

10. The porous lattice structure of claim 9, wherein:
a first node face is located on a lower half of the node;
the sub-unit further comprise a second strut fixed on its proximate end to a second node face and fixed on its distal end to a corner of the cuboid volume nearest to the second node face and the second node face is located on the lower half of the node and opposite the first node face;
the sub-unit further comprise a third strut fixed on its proximate end to a third node face and fixed on its distal end to a corner of the cuboid volume nearest to the third node face, and the third node face is located on an upper half of the node and about 90 degrees laterally from the first node face; and
the sub-unit cells further comprise a fourth strut, fixed on its proximate end to a fourth node face and, fixed on its distal end to a corner of the cuboid volume nearest to the fourth node face, and the fourth node face is located on upper half of the octahedron volume and opposite the third node face.

11. The porous lattice structure of claim 10, wherein the unit cells further comprise a first grouping of four sub-unit cells fixed to a second grouping of four sub-unit cells, the first grouping comprising four substantially similar sub-unit cells, arranged and fixed laterally in a rectangle when viewed from above, and the second grouping comprising four substantially similar sub-unit cells inverted relative to the first grouping and fixed laterally in a rectangle when viewed from above.

12. The porous lattice structure of claim 1, wherein node has a volumetric density of less than 100 percent.

13. The porous lattice structure of claim 1, wherein the cuboid volume comprises a plurality of struts having a plurality of strut directions and meeting at a plurality of vertices, the strut directions defining a plurality of rhombic openings and the plurality of vertices defining corners of the rhombic openings, wherein each vertex of the plurality of vertices comprises an internal angle defined by a strut direction of two struts that meet at that vertex and at least one rhombic opening comprises two internal angles that equal a lateral separation angle ranging between 109.5 degrees and 180 degrees.

14. The porous lattice structure of claim 13, wherein lattice structure comprises a rhombic dodecahedron.

15. The porous lattice structure of claim 14, wherein lattice structure further comprises a second plurality of struts extending radially from rhombic dodecahedron and contained within cuboid volume.

16. The porous lattice structure of claim 13, wherein lattice structure comprises a radial dodeca-rhombus.

17. The porous lattice structure of claim 13, wherein lateral separation angle ranges between and including 111 degrees and 120 degrees.

18. The porous lattice structure of claim 13, wherein a line bisecting an internal angle at one vertex of a rhombic opening is perpendicular to a first direction of loading; wherein the elastic modulus of porous structure in the first direction of loading is between and including 0.375 GPa to 4 GPa; and wherein the volumetric density of porous structure is between and including 5 percent to 40 percent.

19. The porous structure of claim 18, wherein elastic modulus is a design elastic modulus.

20. The porous structure of claim 18, wherein elastic modulus is an actual elastic modulus.

21. The porous structure of claim 20, further comprising a volumetric density of between and including 30 percent to 38 percent.

22. The porous structure of claim 13, wherein a line bisecting an internal angle at one vertex of a rhombic opening is perpendicular to a first direction of loading and further comprising:
a second direction of loading oriented at an angle offset from first direction of loading,
wherein the elastic modulus along the first direction of loading is between and including 0.3 GPa to 12 GPa;
wherein the elastic modulus along a second direction of loading is between and including 2 GPa to 25 GPa; and
wherein elastic modulus along the first direction of loading is less than elastic modulus along a second direction of loading.

* * * * *